United States Patent
Yu et al.

(10) Patent No.: US 10,271,722 B2
(45) Date of Patent: Apr. 30, 2019

(54) IMAGING TO FACILITATE OBJECT OBSERVATION

(71) Applicant: BEIJING ZHIGU RUI TUO TECH CO., LTD., Beijing (CN)

(72) Inventors: Kuifei Yu, Beijing (CN); Lin Du, Beijing (CN); Wei Shi, Beijing (CN)

(73) Assignee: BEIJING ZHIGU RUI TUO TECH CO., LTD., Beijing (CN)

( * ) Notice: Subject to any disclaimer, the term of this patent is extended or adjusted under 35 U.S.C. 154(b) by 500 days.

(21) Appl. No.: 14/905,253

(22) PCT Filed: Jul. 2, 2014

(86) PCT No.: PCT/CN2014/081486
§ 371 (c)(1),
(2) Date: Jan. 14, 2016

(87) PCT Pub. No.: WO2015/043274
PCT Pub. Date: Apr. 2, 2015

(65) Prior Publication Data
US 2016/0150950 A1 Jun. 2, 2016

(30) Foreign Application Priority Data
Sep. 30, 2013 (CN) .......................... 2013 1 0462638

(51) Int. Cl.
*A61B 3/00* (2006.01)
*A61B 3/12* (2006.01)
(Continued)

(52) U.S. Cl.
CPC ............ *A61B 3/0025* (2013.01); *A61B 3/103* (2013.01); *A61B 3/113* (2013.01); *A61B 3/12* (2013.01); *A61B 3/14* (2013.01); *G06F 3/013* (2013.01)

(58) Field of Classification Search
CPC ........... A61B 3/12; A61B 3/102; A61B 3/145; A61B 3/0025; A61B 3/14; A61B 3/113; A61B 3/103
(Continued)

(56) References Cited

U.S. PATENT DOCUMENTS

| 6,120,461 A | 9/2000 | Smyth | |
|---|---|---|---|
| 2002/0113943 A1* | 8/2002 | Trajkovic | G02B 7/102 351/209 |
| 2015/0177834 A1* | 6/2015 | Karakotsios | G06F 3/013 345/156 |

FOREIGN PATENT DOCUMENTS

| CN | 101141567 A | 3/2008 |
|---|---|---|
| CN | 101943982 A | 1/2011 |

(Continued)

OTHER PUBLICATIONS

PCT International Search Report and Written Opinion dated Oct. 14, 2014, issued in corresponding International Application No. PCT/CN2014/081486 (9 pages).

*Primary Examiner* — Evan P Dzierzynski
*Assistant Examiner* — Mitchell T Oestreich
(74) *Attorney, Agent, or Firm* — Sheppard Mullin Richter & Hampton LLP

(57) ABSTRACT

To facilitate observation of object(s), an imaging process can include or an imaging device can perform detecting a position of a focusing point of an eye of a user, determining, according to the position of the focusing point, an object gazed by the user, and changing a size of target imaging of the gazed object on the fundus of the user according to a predetermined zooming rule. The size of the target imaging of the gazed object on the fundus of the user can be automatically changed by optical zooming processing, so that the user can observe the gazed object at a modest distance and with a moderate size of the imaging on the (Continued)

fundus, and therefore it may be convenient for the user to observe the gazed object.

30 Claims, 17 Drawing Sheets

(51) Int. Cl.
*A61B 3/14* (2006.01)
*G06F 3/01* (2006.01)
*A61B 3/103* (2006.01)
*A61B 3/113* (2006.01)

(58) Field of Classification Search
USPC ......................................................... 351/206
See application file for complete search history.

(56) References Cited

FOREIGN PATENT DOCUMENTS

| | | |
|---|---|---|
| CN | 102445756 A | 5/2012 |
| CN | 103499886 A | 1/2014 |

\* cited by examiner

IMAGING TO FACILITATE OBJECT OBSERVATION

CROSS-REFERENCE TO RELATED APPLICATION

This application is a national stage application of International Application No. PCT/CN2014/081486, filed on Jul. 2, 2014, which claims priority to and benefits of Chinese Patent Application No. 201310462638.2, filed on Sep. 30, 2013, and entitled "IMAGING DEVICE AND METHOD", The contents of both of the above-referenced applications are incorporated herein by reference in their entirety.

TECHNICAL FIELD

The present application relates to the field of imaging, and in particular, to imaging to facilitate observation of object(s).

BACKGROUND

For a user with healthy eyes, when he views a small object or an object far from him, the eyes hardly observe desired details. For example, when people sitting at a relatively distant location watch a ball game, they hardly observe details of body movement and expression of athletes. For a user with an eye problem such as myopia or hyperopia, when he views a small object or an object far from him, it is more difficult to recognize details of the observed object or people. Conversely, when a user views a large object or an object near him, the user hardly observes global information of the gazed object. For example, when a user stands in front of a tall building or a mountain, he hardly observes the overall situation.

A traditional optical zoom device, such as a telescope or a magnifying glass, is not convenient to use because zooming parameters are required to be set manually.

SUMMARY

The following presents a simplified summary in order to provide a basic understanding of some aspects disclosed herein. This summary is not an extensive overview. It is intended to neither identify key or critical elements nor delineate the scope of the aspects disclosed. Its sole purpose is to present some concepts in a simplified form as a prelude to the more detailed description that is presented later.

An example purpose of at least one embodiment in the present application is to provide an imaging device and method to make it convenient for a user to observe a gazed object.

According to an example embodiment of the present application, a method comprises:

detecting, by a system comprising a processor, a position of a focusing point of an eye of a user;

determining, according to the position of the focusing point, a gazed object gazed by the user; and changing a size of target imaging of the gazed object on a fundus of the user according to a predetermined zooming rule.

According to another example embodiment of the present application, An imaging device, comprising:

a processor that executes or facilitates execution of executable units to perform operations of the imaging device, the executable units comprising:

a detection unit configured to detect a position of a focusing point of an eye of a user;

an object determining unit configured to determine, according to the position of the focusing point, a gazed object at which the user is determined to be gazing; and a processing unit configured to change a size of target imaging of the gazed object on a fundus of the user according to a predetermined zooming rule.

According to another example embodiment of the present application, a computer-readable storage device, comprising at least one executable instruction, which, in response to execution, causes an imaging device comprising a processor to perform operations, comprising:

detecting a position of a focusing point of an eye of a user;

determining, according to the position of the focusing point, an object gazed at by the user, and changing a size of target imaging of the object on a fundus of the user according to a predetermined zooming rule.

According to another example embodiment of the present application, an imaging device is provided, comprising a processor and a memory, wherein the memory stores at least one executable instruction, the processor is connected to the memory via a communication bus, and when the imaging device is in operation, the processor executes or facilitates execution of the at least one executable instruction stored in the memory, to cause the imaging device to execute operations, comprising:

detecting a position of a focusing point of an eye of a user;

determining, according to the position of the focusing point, a gazed object at which the user has been determined to be gazing; and changing a size of target imaging of the gazed object on a fundus of the user according to a predetermined zooming rule.

In the device and method according to at least one embodiment of the present application, an object gazed by a user is determined according to a position of a focusing point of an eye of the user, and a size of target imaging of the gazed object on the fundus of the user is changed according to a predetermined zooming rule, so that the user can observe the gazed object at a moderate distance and with a moderate size of the imaging on the fundus, and therefore it may be convenient for the user to observe the gazed object, thereby improving the observing efficiency.

DETAILED DESCRIPTION

The specific implementation manners of the present application are further described below in detail with reference to the accompanying drawings and embodiments. The following embodiments are used to describe the present application, but not used to restrict the scope of the present application.

When an object is small or an object is far away from the eye of a user, imaging on the fundus of the user is small, and in this case the user expects to get the object closer for viewing; and when the object is larger or closer, the user hardly observes global information thereof, and in this case the user expects to get the object far away for viewing. Therefore, according to at least one embodiment of the present application, an imaging method is provided to automatically change a size of target imaging of an object on the fundus of the user by optical zooming processing, so that it may be convenient for the user to view a gazed object.

Figure 1:
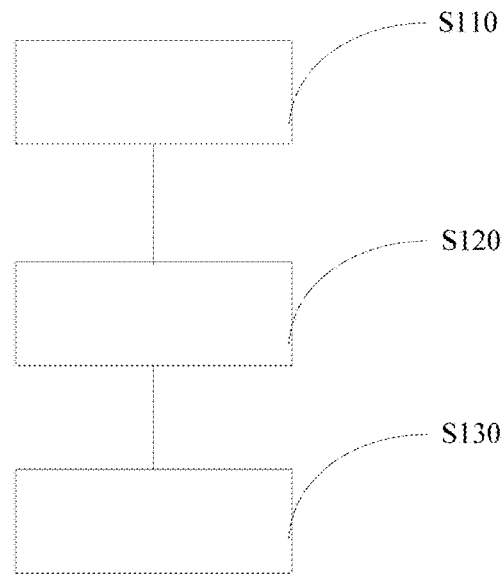
FIG. 1 shows an example flowchart of an imaging method according to an embodiment of the present application.

As shown in FIG. 1, the method comprises:

S110: Detect a position of a focusing point of an eye of a user.

Here, the position of the focusing point of the eye of the user is a spatial position that is determined by both of an equivalent focal length and a direction of line-of-sight of the eye, and this position corresponds to a current gazed object of the user. Therefore, the gazed object of the user may be determined by detecting this position.

S120: Determine, according to the position of the focusing point, an object gazed by the user.

The object at the position of the focusing point may be a large object, or may be multiple objects existing at the same time. Especially when the position of the focusing point is far from the eye of the user, for example, when the user is watching 100 m away a football player running with a ball, the object gazed by the user needs to be further distinguished and determined by some existing image processing technologies, which is not the key point of the present application and is not described again here.

S130: Change a size of target imaging of the gazed object on the fundus of the user according to a predetermined zooming rule.

In this step, changing the size of the target imaging of the gazed object on the fundus of the user is mainly implemented by optical zooming processing. The changing the size of the target imaging of the gazed object on the fundus of the user may be optical zoom-in of the target imaging of the gazed object on the fundus of the user, or may be optical zoom-out of the target imaging of the gazed object on the fundus of the user. There are many situations for the predetermined zooming rule, for example, the size of the target imaging of the gazed object on the fundus of the user may be changed according to an actual area proportion of the target imaging on the fundus of the user, or the size of the target imaging of the gazed object on the fundus of the user may be changed according to a distance from the gazed object to the eye. The predetermined zooming rule should be set to allow the user to feel comfort when observing the gazed object by using an area proportion of the target imaging on the fundus of the user after the size of the target imaging is changed.

The method may be implemented by, for example, an imaging device (for example, an eyeglass), and the imaging device is arranged between the eye of the user and the gazed object, and intersects with the direction of line-of-sight of the user. In the step S130, the imaging device is used to perform optical zooming processing on the gazed object so as to change the size of the target imaging of the gazed object on the fundus of the user.

In the method according to the embodiment, an object gazed by a user is determined according to a position of a focusing point of an eye of the user, and a size of target imaging of the gazed object on the fundus of the user is changed according to a predetermined zooming rule, so that the user can observe the gazed object at a moderate distance and with a moderate size of the imaging on the fundus, and therefore it may be convenient for the user to observe the gazed object.

Specifically, in the step S110, the position of the focusing point of the eye of the user may be determined according to an intersection point of sight lines of two eyes, wherein the embodiment further provides a method configured to determine a position of a focusing point of an eye of a user according to an actual focus distance and a direction of line-of-sight of the eye. The step S110 may comprise:

S111: Collect images on the fundus of the user.

S112: Adjust imaging parameters of an optical path between the eye and an image collecting position so as to collect images with the definition greater than a preset value.

S113: Process the collected images to obtain an equivalent focal length and a direction of line-of-sight of the eye that are corresponding to the images with the definition greater than the preset value. This step specifically comprises:

analyzing the collected images to find out the images with the definition greater than the preset value; and calculating the equivalent focal length and the direction of line-of-sight of the eye according to the images with the definition greater than the preset value and known imaging parameters of the optical path corresponding to the images with the definition greater than the preset value.

Here, in the step S113, for the purpose of increasing the precision, the equivalent focal length and the direction of line-of-sight of the eye may be calculated according to an image with the highest definition and the known imaging parameters of the optical path corresponding to the image with the highest definition.

S114: Obtain an actual focus distance of the eye according to the equivalent focal length of the eye.

S115: Obtain the position of the focusing point according to the direction of line-of-sight and the actual focus distance.

In addition, in order to avoid the change of imaging on the fundus of the user under a non-gazing state of the user, for example, in a random glancing process, to influence the user experience, the step S130 preferably comprises:

S130': In the case where the user observes the gazed object for a duration exceeding a preset duration, change the size of the target imaging of the gazed object on the fundus of the user according to the predetermined zooming rule.

Here, the preset duration is set to just determine the observed object gazed by the user is the target. Generally, if human eyes want to obtain a visual impression when looking at a target, the shortest observing time is 0.07-0.3 s, and the preset duration should be greater than the shortest observing time, for example, may be set as 1 s, 2 s, or the like. In addition, the duration of the user observing the gazed object may be acquired by monitoring the duration of the focusing point of the eye of the user keeping at a constant position, that is, when the duration of the focusing point of the eye of the user keeping at a constant position exceeds the preset duration, it may be determined that the user is gazing the object at the position of the focusing point; or may be acquired by monitoring a gaze duration of imaging at the central fovea of the macula lutea, that is, when the gaze duration of the imaging of a same object at the central fovea exceeds the preset duration, it may be determined that the user is currently gazing this object.

The method is described below by implementation manners for the multiple situations of the predetermined zooming rule:

In a first implementation manner of the method according to the embodiment, the method further comprises:

S140a: Preset a target focus distance of the eye of the user and a buffer of the target focus distance;

Correspondingly, the step S130 comprises:

S130a: Change the size of the target imaging according to the target focus distance, the actual focus distance and the buffer.

Specifically, in the step S140a, the target focus distance is an expected focus distance of the eye of the user, that is, an expected value of a viewing distance of the user observing the gazed object, for example, may be 10 m. When an actual focus distance of the eye of the user, that is, an actual viewing distance, is the target focus distance, the user may feel that the gazed object is at a modest distance and the imaging on the fundus is not large or small. In addition, the target focus distance at which the user feels comfort is not generally a distance point, and is more likely a distance range. Therefore, in the step S140a, a buffer of the target focus distance is further arranged. Generally, the buffer of the target focus distance is predetermined distance ranges at two sides of the target focus distance. For example, given that the target focus distance is $D_T$, the buffer may be $((D_T-D_L, D_T) \cup (D_T, D_T+D_R))$, wherein, $D_T$, $D_L$ and $D_R$ are constants. Therefore, the focus distance range $(D_T-D_L, D_T+D_T)$ is set to be a focus distance range in which the user feels comfort. $D_L$ may be equal to $D_R$, and in this case, a third sub-buffer $((D_T-D_L, D_T)$ and a fourth sub-buffer $(D_T, D_T+D_R)$ in the buffer of the target focus distance are the same in size, and take $D_T$ as the center; and $D_L$ may be not equal to $D_R$, and in this case, the third sub-buffer $((D_T-D_L, D_T)$ and the fourth sub-buffer $(D_T, D_T+D_R)$ are different in size.

The step S130a comprises:

In the case where the actual focus distance is less than the target focus distance, and the actual focus distance is outside the buffer of the target focus distance, increasing the actual focus distance to the target focus distance to zoom out the target imaging; and in the case where the actual focus distance is greater than the target focus distance, and the actual focus distance is outside the buffer of the target focus distance, reducing the actual focus distance to the target focus distance to zoom in the target imaging.

In some implementation manners requiring simple control, the buffer of the target focus distance may also be set to zero, which is equivalent to that the buffer of the target focus distance is not set, and in this case, the step S130a comprises:

in the case where the actual focus distance is less than the target focus distance, increasing the actual focus distance to the target focus distance to zoom out the target imaging; and in the case where the actual focus distance is greater than the target focus distance, reducing the actual focus distance to the target focus distance to zoom in the target imaging.

In a second implementation manner of the method according to the embodiment, the step S130 comprises:

S131b: Calculate an actual area proportion of the target imaging on the fundus of the user.

S132b: Determine a corresponding magnification factor according to the actual area proportion.

S133b: Change the size of the target imaging according to the magnification factor.

Specifically, in the step S131b, the area of the fundus of the user is generally a fixed value, and after the image on the fundus of the user is collected, the imaging on the central foveal of the macula lutea may be extracted to be used as the target imaging, so as to further acquire the area of the target imaging and then to obtain the actual area proportion of the target imaging on the fundus of the user.

In the step S132b, the corresponding magnification factor may be determined according to the actual area proportion in multiple implementation manners, for example, the corresponding magnification factor is determined according to a piecewise function corresponding to the actual area proportion or by table look-up. In this implementation manner, a quick table look-up manner is selected, that is, a table of correspondence between the actual area proportion and the magnification factor is preset, and then during execution of the method, the current required magnification factor is determined by table look-up. Here, the magnification factor may be 1, or may be a constant greater than 1, or may be a fraction greater than zero and less than 1. Table 1 below is an example of a magnification factor table, and it can be seen that, corresponding to each actual area proportion $S_{RE}$, a preset magnification factor $T_1$ is stored in Table 1, for example, when the actual area proportion $S_{RE}$ is 20%, it may be determined by table look-up that the corresponding magnification factor is 2.

TABLE 1

First Magnification Factor Table

| Actual area proportion $S_{RE}$ | Magnification factor $T_1$ |
| --- | --- |
| $0 < S_{RE} \leq 5\%$ | 15 |
| $5\% < S_{RE} \leq 10\%$ | 6 |
| $10\% < S_{RE} \leq 30\%$ | 2 |
| $30\% < S_{RE} \leq 70\%$ | 1 |
| $70\% < S_{RE} \leq 90\%$ | 2/3 |
| $90\% < S_{RE} \leq 100\%$ | 1/2 |

In the step S133b, the imaging of the gazed object on the fundus of the user is generally magnified to the magnification factor determined in the step S132b in a manner of adjusting a focal length of an optical lens. For example, when the actual area proportion $S_{RE}$ of the target imaging (that is, an initial area proportion of the target imaging of the gazed object on the fundus of the user) is 20%, and when the magnification factor is determined to be 2 in the step S132b, after the optical zooming processing in the step S133b, the area proportion of the new imaging of the gazed object on the fundus of the user is 40%; when the actual area proportion $S_{RE}$ of the target imaging is 50%, and when the magnification factor is determined to be 1 in the step S132b, no optical zooming processing is performed in the step S133b, and the area proportion of the imaging of the gazed object on the fundus of the user is not changed; and when the actual area proportion $S_{RE}$ of the target imaging is 98%, and when the magnification factor is determined to be ½ in the step S132b, after the optical zooming processing in the step S133b, the area proportion of the new imaging of the gazed object on the fundus of the user is 49%.

It can be seen that after the above zooming processing, the large or small actual area proportion of the target imaging of the gazed object on the fundus of the user is adjusted to be a moderate proportion, so that it may be convenient for the user to view the gazed object. In addition, in the above steps S132b and S133b, it may be set to perform zooming processing only when the actual area proportion of the target imaging is excessively small (for example, less than 30%), or may be set to perform zooming processing only when the actual area proportion of the target imaging is excessively large (for example, greater than 70%).

In a third implementation manner of the method according to the embodiment, the step S130 comprises:

S131c: Acquire a viewing distance from the gazed object to the eye of the user.

S132c: Determine a corresponding magnification factor according to the viewing distance.

S133c: Change the size of the target imaging according to the magnification factor.

Specifically, in the step S131c, the actual focus distance may be used as the viewing distance from the gazed object to the eye of the user.

In addition, in the step S131c, the viewing distance from the gazed object to the eye of the user may be acquired in the following manners:

tracing the direction of line-of-sight of the eye of the user, acquiring a scene depth of the position of the gazed object according to the direction of line-of-sight, and calculating the viewing distance from the gazed object to the eye of the user according to the scene depth; or tracing direction of line-of-sight of two eyes of the user, and obtaining the viewing distance from the gazed object to the eye of the user according to an intersection point of the direction of line-of-sight of the two eyes of the user.

The step S132c may comprise multiple implementation manners, for example, the corresponding magnification factor is determined according to a piecewise function corresponding to the viewing distance or by table look-up. In this implementation manner, a quick table look-up manner is selected, that is, a table of correspondence between the viewing distance and the magnification factor is preset, and then during execution of the method, the current required magnification factor is determined by table look-up. Here, the magnification factor may be 1, or may be a constant greater than 1, or may be a fraction greater than zero and less than 1. Table 2 below is an example of a magnification factor table, and it can be seen that, corresponding to each viewing distance $D_O$, a preset magnification factor $T_2$ is stored in Table 2, for example, when the viewing distance $D_O$ is 20 m, it may be determined by table look-up that the corresponding magnification factor is 5.

TABLE 2

Second Magnification Factor Table

| Viewing Distance $D_O$ (unit: m) | Magnification factor $T_2$ |
| --- | --- |
| $D_O > 100$ | 10 |
| $10 < D_O \leq 100$ | 5 |
| $1 < D_O \leq 10$ | 2 |
| $0.3 < D_O \leq 1$ | 1 |
| $0.1\ D_O \leq 0.3$ | 2/3 |
| $0 < D_O \leq 0.1$ | 1/2 |

In the step S133c, the imaging of the gazed object on the fundus of the user is generally magnified to the magnification factor determined in the step S132c in a manner of optical zooming. For example, when the viewing distance from the gazed object to the eye of the user is 20 m, and when the magnification factor is determined to be 2 in the step S132c, after optical zooming processing in the step S133c, the area proportion of the new imaging of the gazed object on the fundus of the user may be two times of that before zooming; when the viewing distance from the gazed object to the eye of the user is 0.5 m, and when the magnification factor is determined to be 1 in the step S132c, no optical zooming processing is performed in the step S133c, and the area proportion of the imaging of the gazed object on the fundus of the user is not changed; and when the viewing distance from the gazed object to the eye of the user is 0.1 m, and when the magnification factor is determined to be ½ in the step S132c, after the optical zooming processing in the step S133c, the area proportion of the new imaging of the gazed object on the fundus of the user is half of that before zooming.

According to the visual principle of "big when close, small when far", when the viewing distance from the gazed object to the eye of the user is large, the target imaging of the gazed object on the fundus of the user is small, and when the viewing distance from the gazed object to the eye of the user is small, the target imaging of the gazed object on the fundus of the user is large. It can be seen that after the above zooming processing, when the viewing distance is large, the target imaging is magnified, which is equivalent to zoom in the gazed object to view; and when the viewing distance is small, the target imaging is reduced, which is equivalent to zoom out the gazed object to view. Therefore, the large or small actual area proportion of the target imaging of the gazed object on the fundus of the user is adjusted to be a moderate proportion, so that it may be convenient for the user to view the gazed object. In addition, in the above steps S132c and S133c, it may be set to perform zooming processing only when the viewing distance is excessively large (for example, greater than 10 m), or may be set to perform zooming processing only when the viewing distance is excessively small (for example, less than 0.1 m).

In a fourth implementation manner of the method according to the embodiment, the method further comprises:

S140d: Preset a target area proportion of the target imaging and a buffer of the target area proportion.

Moreover, the step S130 comprises:

S131d: Calculate an actual area proportion of the target imaging on the fundus of the user.

S132d: Change the size of the target imaging according to the target area proportion, the actual area proportion and the buffer.

Specifically, in the step S140d, the target area proportion is an expected area proportion of the target imaging on the fundus of the user, for example, may be 50%. When the area proportion of the target imaging on the fundus of the user is the target area proportion, the user may feel that the gazed object is at a modest distance and the target imaging is not large or small. In addition, the area proportion of the target imaging at which the user feels comfort is not generally an area proportion point, and is more likely an area proportion range. Therefore, a buffer of the target area proportion is further arranged in the step S140d. Generally, the buffer is predetermined area proportion ranges at two sides of the target area proportion. For example, given that the target area proportion is $S_T$, the buffer may be $((S_T-S_L, S_T) \cup (S_T, S_T+S_R))$, wherein, $S_T$, $S_L$ and $S_R$ are constants. Therefore, the area proportion range $(S_T-S_L, S_T+S_R)$ is set to be an area proportion range in which the user feels comfort. $S_L$ may be equal to $S_R$, and in this case, a first sub-buffer $(S_T-S_L, S_T)$ and a second sub-buffer $(S_T, S_T+S_R)$ in the buffer are same in size, and take $S_T$ as the center; and $S_L$ may be not equal to $S_R$, and in this case, the first sub-buffer $(S_T-S_L, S_T)$ and the second sub-buffer $(S_T, S_T+S_R)$ are different in size.

In the step S131d, the area of the fundus of the user is generally a fixed value, and after the image on the fundus of the user is collected, the imaging on the central foveal of the macula lutea may be extracted to be used as the target imaging, so as to further acquire the area of the target imaging and then to obtain the actual area proportion of the target imaging on the fundus of the user.

The step S132d comprises:

In the case where the actual area proportion is less than the target area proportion, and the actual area proportion is outside the buffer, magnifying the target imaging to the target area proportion; and in the case where the actual area proportion is greater than the target area proportion, and the actual area proportion is outside the buffer, reducing the target imaging to the target area proportion.

In some implementation manners requiring simple control, the buffer may be set to zero, which is equivalent to that the buffer is not set, and in this case, the step S132d comprises:

in the case where the actual area proportion is less than the target area proportion, magnifying the target imaging to the target area proportion; and in the case where the actual area proportion is greater than the target area proportion, reducing the target imaging to the target area proportion.

It can be seen that, in addition to magnifying the imaging of the far and small gazed object on the fundus of the user, the method may also reduce the imaging of the near and large gazed object on the fundus of the user, so as to relieve eye fatigue of the user in different usage scenarios.

It should be understood that, in the embodiments of the present invention, the sequence numbers of the above processes do not imply an execution sequence, and the execution sequence of the processes should be determined according to the functions and internal logic, which is not intended to limit the implementation processes of the embodiments of the present invention in any way.

In summary, in the method according to the embodiment, an object gazed by a user is determined according to a position of a focusing point of an eye of the user, and a size of target imaging of the gazed object on the fundus of the user is automatically changed by optical zooming processing according to the size of the target imaging of the gazed object on the fundus of the user or according to a viewing distance from the gazed object to the eye of the user, so that the user can observe the gazed object at a modest distance and with a moderate size of the imaging on the fundus, and therefore it is convenient for the user to observe the gazed object, thereby improving the observing efficiency.

In addition, the embodiment of the present application further provides a computer-readable medium, comprising a computer readable instruction when the following operations are executed: executing operations of steps S110, S120 and S130 of the method in the embodiment shown in the above FIG. 1.

Figure 2A:
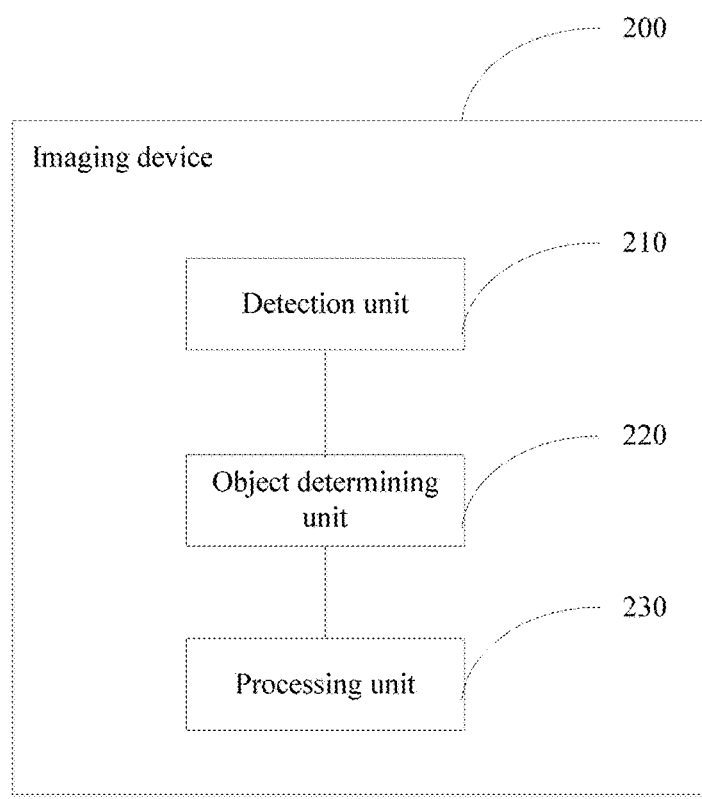
FIG. 2a shows an example schematic diagram of a module structure of an imaging device according to an embodiment of the present application.

FIG. 2a shows a schematic diagram of a module structure of an imaging device according to an embodiment of the present application. The imaging device is arranged between an eye of a user and a gazed object, and intersects with a direction of line-of-sight of the user. As shown in FIG. 2a, the device 200 comprises: a detection unit 210, an object determining unit 220 and a processing unit 230.

The detection unit 210 is configured to detect a position of a focusing point of an eye of a user.

The object determining unit 220 is configured to determine, according to the position of the focusing point, an object gazed by the user.

The processing unit 230 is configured to change a size of target imaging of the gazed object on the fundus of the user according to a predetermined zooming rule.

In the imaging device according to the embodiment, an object gazed by a user is determined according to a position of a focusing point of an eye of the user, and a size of target imaging of the gazed object on the fundus of the user is changed according to a predetermined zooming rule, so that the user can observe the gazed object at a moderate distance and with a moderate size of the imaging on the fundus, and therefore it may be convenient for the user to observe the gazed object.

Figure 2B:
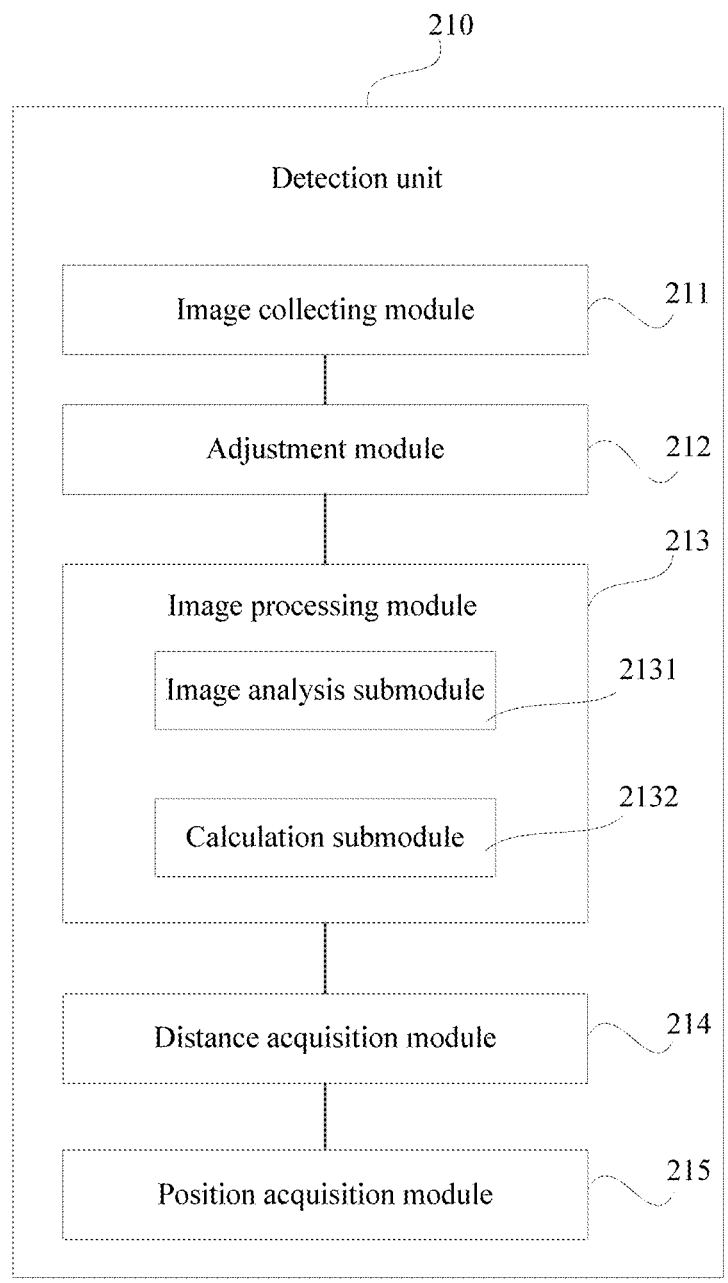
FIG. 2b shows an example schematic diagram of a module structure of a detection unit according to an embodiment of the present application.

Specifically, referring to FIG. 2b, the detection unit 210 may comprise:

an image collecting module 211 configured to collect images on the fundus of the user;

an adjustment module 212 configured to adjust imaging parameters of an optical path between the eye and the image collecting module to collect images with the definition greater than a preset value;

an image processing module 213 configured to process the collected images to obtain an equivalent focal length and a direction of line-of-sight of the eye that are corresponding to the images with the definition greater than the preset value;

a distance acquisition module 214 configured to obtain an actual focus distance of the eye according to the equivalent focal length of the eye; and a position acquisition module 215 configured to obtain the position of the focusing point according to the direction of line-of-sight and the actual focus distance.

Here, the image processing module 213 comprises:

an image analysis submodule 2131 configured to analyze the collected images to find out the images with the definition greater than the preset value; and a calculation submodule 2132 configured to calculate the equivalent focal length and the direction of line-of-sight of the eye according to the images with the definition greater than the preset value and known imaging parameters of the optical path corresponding to the images with the definition greater than the preset value.

Here, for the purpose increasing the precision, the image analysis submodule 2131 may select an image with the highest definition from the images with the definition greater than the preset value, and the calculation submodule 2132 may calculate the equivalent focal length and the direction of line-of-sight of the eye according to the image with the highest definition and the known imaging parameters of the optical path corresponding to the image with the highest definition.

Figure 3A:
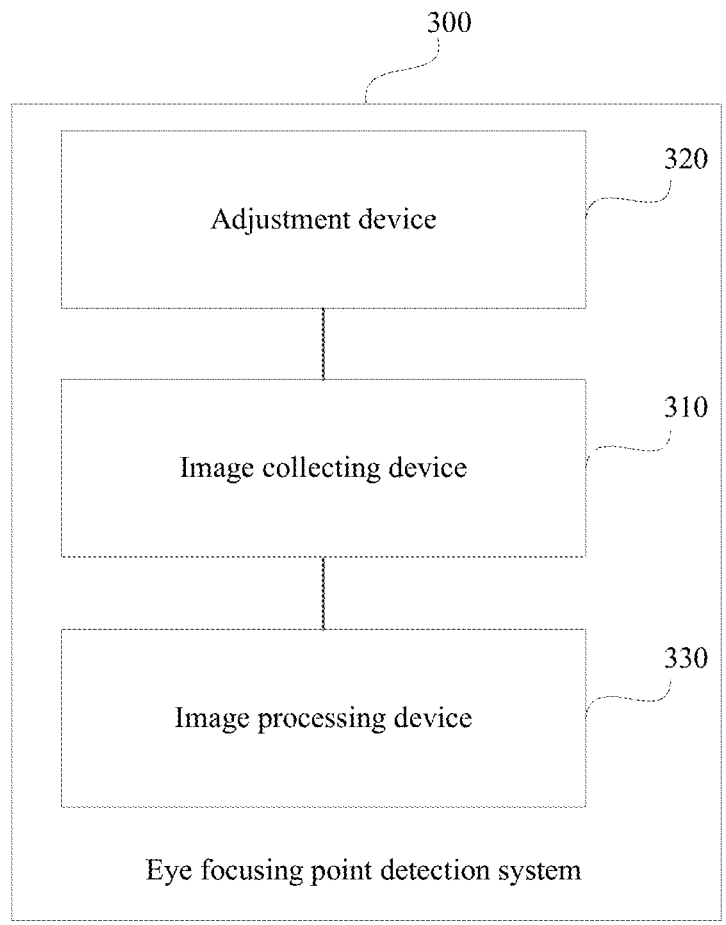
FIG. 3a shows an example schematic diagram of a module structure of an eye focusing point detection system according to an embodiment of the present application.

Substantially, the detection unit 210 may be implemented by using an eye focusing point detection system, as shown in FIG. 3a. The eye focusing point detection system 300 may comprise:

an image collecting device 310 configured to collect an image presented on the fundus;

an adjustment device 320 configured to adjust the imaging parameters between the eye and the image collecting device 310 to allow the image collecting device 310 to obtain the images with the definition greater than the preset value; and an image processing device 330 configured to process the images obtained by the image collecting device 310 to obtain optical parameters of the eye corresponding to the images with the definition greater than the preset value.

The system 300 performs analysis processing for the image on the fundus of the user to obtain the optical parameters of the eye corresponding to the images with the definition greater than the preset value, so as to calculate the current position of the focusing point of the eye.

Here, the image presented at the "fundus" is an image presented at the retina, and may be an image of the fundus itself or an image of another object that is projected on the fundus.

Figure 3B:
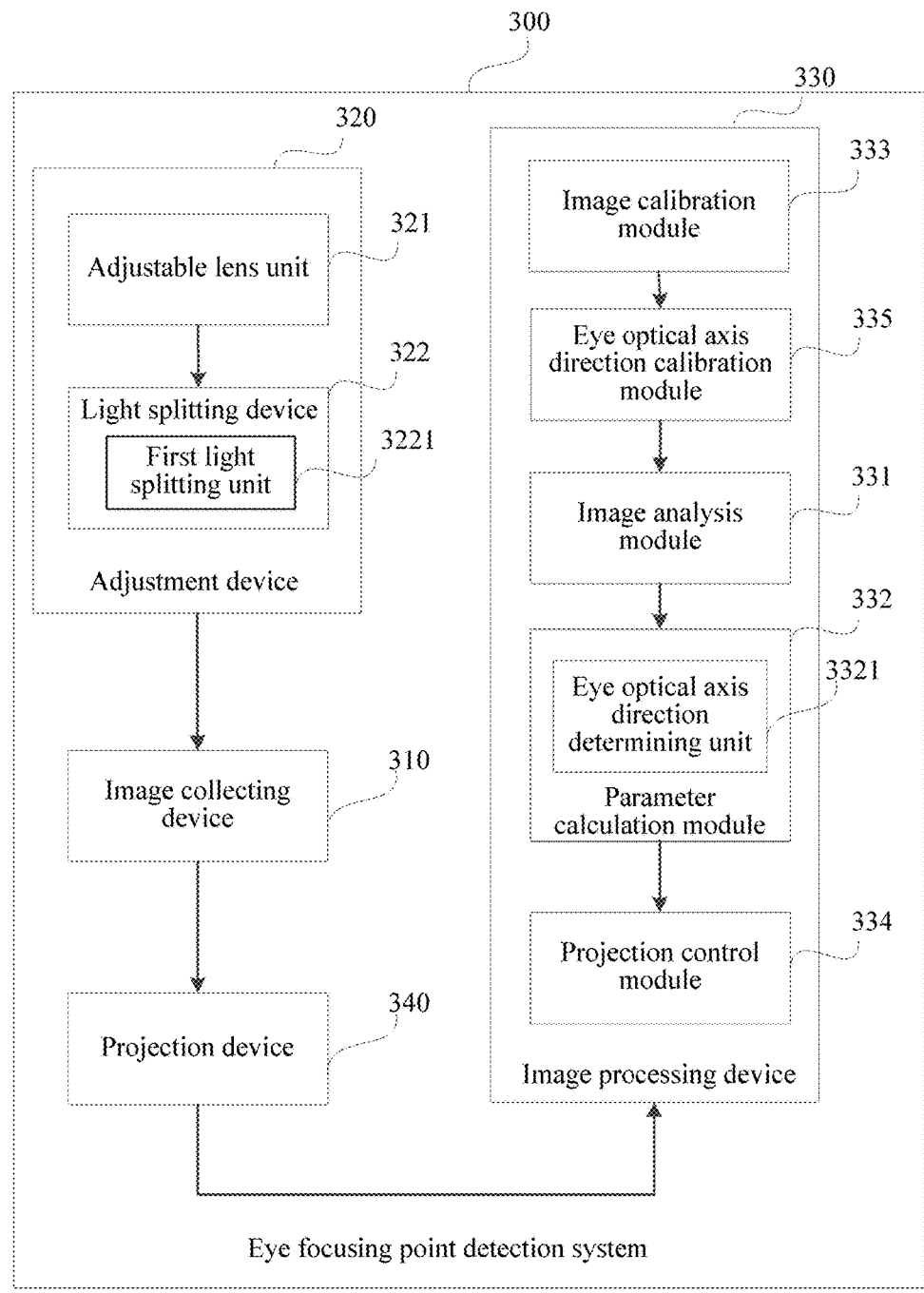
FIG. 3b shows an example schematic diagram of a module structure of a preferable eye focusing point detection system according to an embodiment of the present application.

As shown in FIG. 3b, in a possible implementation manner, the image collecting device 310 is a miniature camera, an in another possible implementation manner according to the embodiment of the present application, the image collecting device 310 may also directly use a photosensitive imaging device, such as a CCD (Charge Coupled Device) or a CMOS (Complementary Metal Oxide Semiconductor).

In a possible implementation manner, the adjustment device 320 comprises: an adjustable lens unit 321, located on an optical path between the eye and the image collecting device 310, with an adjustable focal length and/or an adjustable position in the optical path. Through the adjustable lens unit 321, a system equivalent focal length between the eye and the image collecting device 310 is adjustable, and by the adjustment of the adjustable lens unit 321, the image collecting device 310 may acquire the clearest image on fundus at a certain position or state of the adjustable lens unit 321. In this implementation manner, the adjustable lens unit 321 may perform continuous and real-time adjustment in the detection process.

Here, in a possible implementation manner, the adjustable lens unit 321 may be a lens with an adjustable focal length for accomplishing the adjustment of its focal length by adjusting its refractive index and/or shape. It specifically comprises: 1) adjusting the focal length by adjusting the curvature of at least one surface of the lens with an adjustable focal length, for example, adding or reducing a liquid medium in a cavity formed by a double-layer transparent layer to adjust the curvature of the lens with an adjustable focal length; and 2) adjusting the focal length by changing the refractive index of the lens with an adjustable focal length, for example, adjusting a voltage of an electrode corresponding to a specific liquid crystal medium that is filled in the lens with an adjustable focal length, to adjust the arrangement of the liquid crystal medium so as to change the refractive index of the lens with an adjustable focal length.

In another possible implementation manner, the adjustable lens unit 321 comprises: a lens assembly configured to adjust relative positions of lenses in the lens assembly to accomplish adjustment of the focal length of the lens assembly.

Besides the above two methods configured to change optical path parameters of the system through the properties of the adjustable lens unit 321, the optical path parameters of the system may also be changed by adjusting the position of the adjustable lens unit 321 in the optical path.

Here, in a possible implementation manner, for the purpose of not affecting the viewing experience of the user on the observed object and for the purpose of applying the system portably on a wearable device, the adjustment device 320 may further comprise a light splitting device 322 configured to form light transfer paths between the eye and the observed object and between the eye and the image collecting device 310. In this way, the optical path may be folded to reduce the volume of the system without affecting experiences of other users as far as possible.

Here, in this implementation manner, the light splitting device 322 may comprise a first light splitting unit 3221 that is located between the eye and the observed object and used to transmit the light from the observed object to the eye and transfer the light from the eye to the image collecting device 310.

The first light splitting unit 3221 may be a light splitter, a light-splitting optical waveguide (comprising an optical fiber) or other suitable light splitting devices.

In a possible implementation manner, the image processing device 330 of the system comprises an optical path calibration module configured to calibrate the optical path of the system, for example, performing aligning calibration for the optical axis of the optical path, to ensure the measuring accuracy.

In a possible implementation manner, the image processing device 330 comprises:

an image analysis module 331 configured to analyze the image acquired by the image collecting device to find out images with the definition greater than a preset value; and a parameter calculation module 332 configured to calculate optical parameters of the eye according to the images with the definition greater than the preset value and the known imaging parameters of the system corresponding to the images with the definition greater than the preset value.

In this implementation manner, the images with the definition greater than the preset value may be obtained by the image collecting device 310 by using the adjustment device 320, but it is required to find out the images with the definition greater than the preset value by using the image analysis module 331, and in this case, the optical parameters of the eye may be calculated according to the images with the definition greater than the preset value and the known optical path parameters of the system. The optical parameters of the eye here may comprise an optical axis direction of the eye.

In a possible implementation manner of the embodiment of the present application, the system may further comprise a projection device 340 configured to project a spot on the fundus. In a possible implementation manner, the function of the projection device may be implemented by a mini projector.

The projected spot here may have no specific pattern and is only used for lightening the fundus.

In a preferable implementation manner, the projected spot comprises a feature-rich pattern. The rich features of the pattern may facilitate detection and improve the detection accuracy. A schematic diagram of a spot pattern 350 is shown in FIG. 3e. The pattern may be formed by a spot pattern generator such as ground glass. FIG. 3f shows an image on fundus that is shot when a spot pattern 350 is projected.

In order not to affect the normal viewing of the eye, the spot may be an invisible infrared spot.

In this case, in order to reduce the interference of other spectra:

An emergent surface of the projection device may be provided with an invisible light transmission filter.

An incident surface of the image collecting device may be provided with an invisible light transmission filter.

Here, in a possible implementation manner, the image processing device 330 further comprises:

a projection control module 334 configured to control the brightness of the projected spot of the projection device according to a result obtained by the image analysis module.

For example, the projection control module 334 may adaptively adjust the brightness according to the features of the image obtained by the image collecting device 310. The features of the image here comprise a contrast of image feature, a textural feature, and the like.

Here, a special situation of the control on the brightness of the projected spot of the projection device is the special situation of starting or stopping the projection device, for example, the projection device may be stopped periodically when a user is continuously fixing eye on one spot; and when the fundus of the user is bright enough, a light emitting source may be turned off, and the distance between the current focusing point of sight of the eye and the eye.

In addition, the projection control module 334 may further control the brightness of the projected spot of the projection device according to ambient light.

Here, in a possible implementation manner, the image processing device 330 further comprises: an image calibration module 333 configured to calibrate the images on the fundus to obtain at least one reference image corresponding to the images represented on the fundus.

The image analysis module 331 performs contrast calculation for the images acquired by the image collecting device 330 and the reference image to obtain the images with the definition greater than the preset value. Here, the image with the definition greater than the preset value may be an obtained image with the difference to the reference image less than a threshold. In this implementation manner, the difference between the currently acquired image and the reference image is calculated according to an existing image processing algorithm, for example, according to a classic phase-difference auto-focusing algorithm.

Here, in a possible implementation manner, the parameter calculation module 332 comprises:

an eye optical axis direction determining unit 3321 configured to obtain an eye optical axis direction according to the eye features corresponding to the images with the definition greater than the preset value. The direction of line-of-sight may be obtained according to the eye optical axis direction and a fixed angle between the eye optical axis direction and the direction of line-of-sight.

The eye feature here may be acquired from the images with the definition greater than the preset value, or may be acquired otherwise.

Figure 3C:
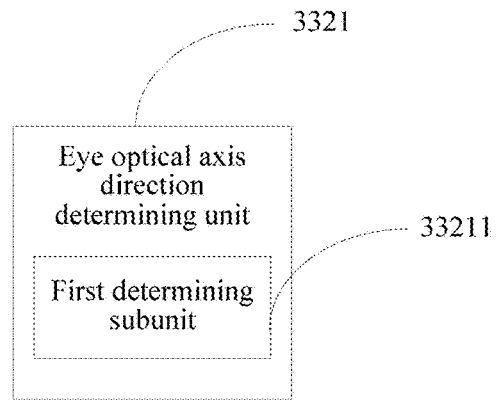
FIG. 3c shows an example schematic diagram of a module structure of an eye optical axis direction determining unit according to an embodiment of the present application.

Here, referring to FIG. 3c, in a possible implementation manner, the eye optical axis direction determining unit 3321 comprises: a first determining subunit 33211 configured to obtain the eye optical axis direction according to the eye features corresponding to the images with the definition greater than the preset value. Compared with obtaining the eye optical axis direction according to the features of pupil and eyeball surface, determining the eye optical axis direction according to the feature of fundus is higher in precision.

When the spot pattern is projected on the fundus, the size of the spot pattern may be greater than a visible area of the fundus or less than a visible area of the fundus, wherein:

When the area of the spot pattern is less than or equal to the visible area of the fundus, the eye optical axis direction may be determined by using a classic matching algorithm of feature points (for example, a scale invariant feature transform (SIFT) algorithm) by detecting the position of the spot pattern on the image relative to the fundus position; and When the area of the spot pattern is greater than or equal to the visible area of the fundus, the direction of line-of-sight of the user may be determined by determining the eye optical axis direction according to the position of the spot pattern on the image relative to the original spot pattern (obtained by an image calibration module).

Figure 3D:
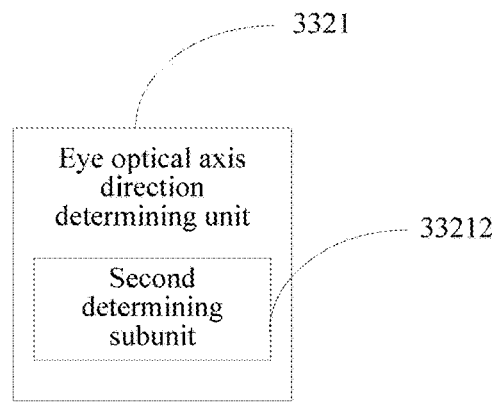
FIG. 3d shows an example schematic diagram of another module structure of an eye optical axis direction determining unit according to an embodiment of the present application.
Figure 3E:
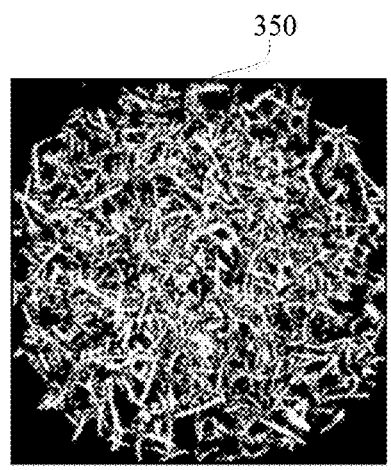
FIG. 3e shows an example schematic diagram of a spot pattern according to an embodiment of the present application.
Figure 3F:
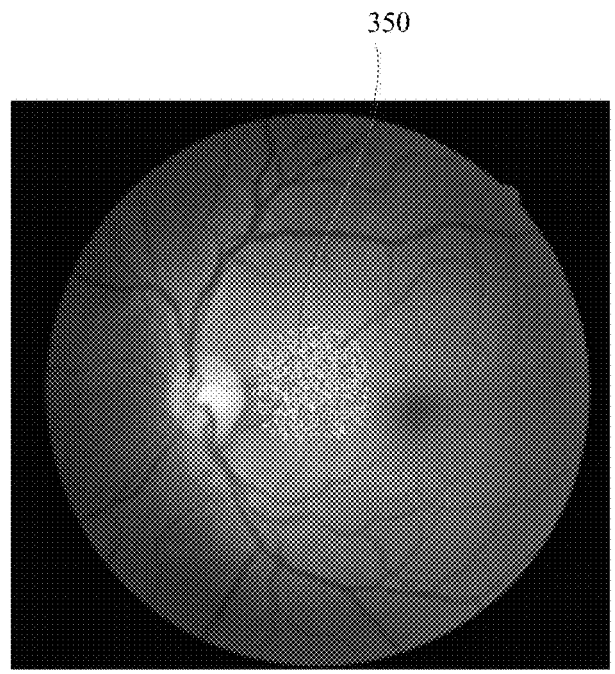
FIG. 3f shows an example image on the fundus that is shot when a spot pattern is projected according to an embodiment of the present application.

Referring to FIG. 3d, in another possible implementation manner, the eye optical axis direction determining unit 3321 comprises: a second determining subunit 33212 configured to obtain the eye optical axis direction according to the eye pupil features corresponding to the images with the definition greater than the preset value. The eye pupil features here may be acquired from the images with the definition greater than the preset value, or may be acquired otherwise. The method configured to obtain the eye optical axis direction through the feature of eye pupil is an existing technology, and therefore no detail is given here.

Here, in a possible implementation manner, the image processing device 330 may further comprise: an eye optical axis direction calibration module 335 configured to calibrate the eye optical axis direction to determine the above eye optical axis direction more accurately.

In this implementation manner, the known imaging parameters of the system comprise a fixed imaging parameter and a real-time imaging parameter, wherein the real-time imaging parameter is parameter information of the adjustable lens unit corresponding to the images with the definition greater than the preset value, and the parameter information may be obtained by recording in the situation of acquiring the images with the definition greater than the preset value.

Figure 3G:
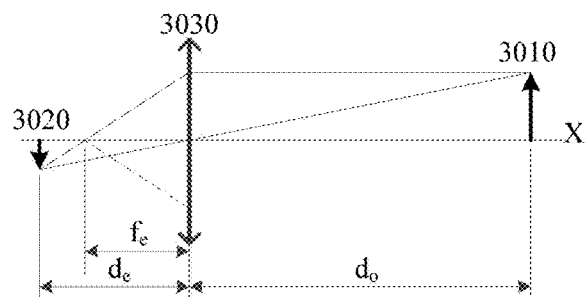
FIG. 3g shows an example schematic diagram of eye imaging according to an embodiment of the present application.

After obtaining the current optical parameters of the eye, the distance from the eye focusing point to the eye may be calculated specifically as follows:

FIG. 3g shows a schematic diagram of imaging of an eye, and formula (1) may be obtained from FIG. 3g in combination with a lens imaging formula in the classic optical theory:

$$\frac{1}{d_o} + \frac{1}{d_e} = \frac{1}{f_e} \tag{1}$$

wherein $d_o$ and $d_e$ are distances between a current observed object 3010 and an eye equivalent lens 3030 and between a real image 3020 at the retina and the eye equivalent lens 3030 respectively, $f_e$ is an equivalent focal length of the eye equivalent lens 3030, and X is a direction of line-of-sight of the eye.

Figure 3H:
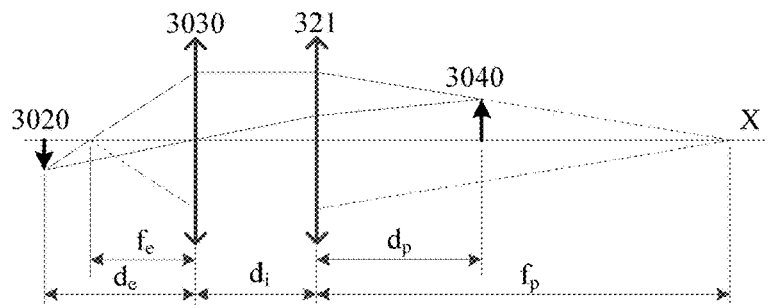
FIG. 3h shows an example schematic diagram of a distance between an eye focusing point and an eye according to known optical parameters of a system and optical parameters of the eye according to the present application.

FIG. 3h shows a schematic diagram of a distance between an eye focusing point and an eye according to known optical parameters of a system and optical parameters of the eye, and a light spot 3040 in FIG. 3h may be converged into a virtual image after passing through the adjustable lens unit 321, and given that the distance from the virtual image to the lens is x, the following equation set may be obtained in combination with formula (1):

$$\begin{cases} \frac{1}{d_p} - \frac{1}{x} = \frac{1}{f_p} \\ \frac{1}{d_i + x} + \frac{1}{d_e} = \frac{1}{f_e} \end{cases} \tag{2}$$

wherein $d_p$ is an optical equivalent distance from the light spot 3040 to the adjustable lens unit 321, $d_i$ is an optical equivalent distance from the adjustable lens unit 321 to the eye equivalent lens 3030, $f_p$ is a focal length value of the adjustable lens unit 321, and $d_i$ is the distance from the eye equivalent lens 3030 to the adjustable lens unit 321.

The distance $d_o$ from the current observed object 3010 (eye focusing point) to the eye equivalent lens 3030 (that is, an actual focus distance of the eye) may be obtained from (1) and (2), as shown in formula (3):

$$d_o = d_i + \frac{d_p \cdot f_p}{f_p - d_p} \tag{3}$$

The position of the focusing point of the eye may be obtained according to the actual focus distance and the direction of line-of-sight of the eye.

Figure 4:
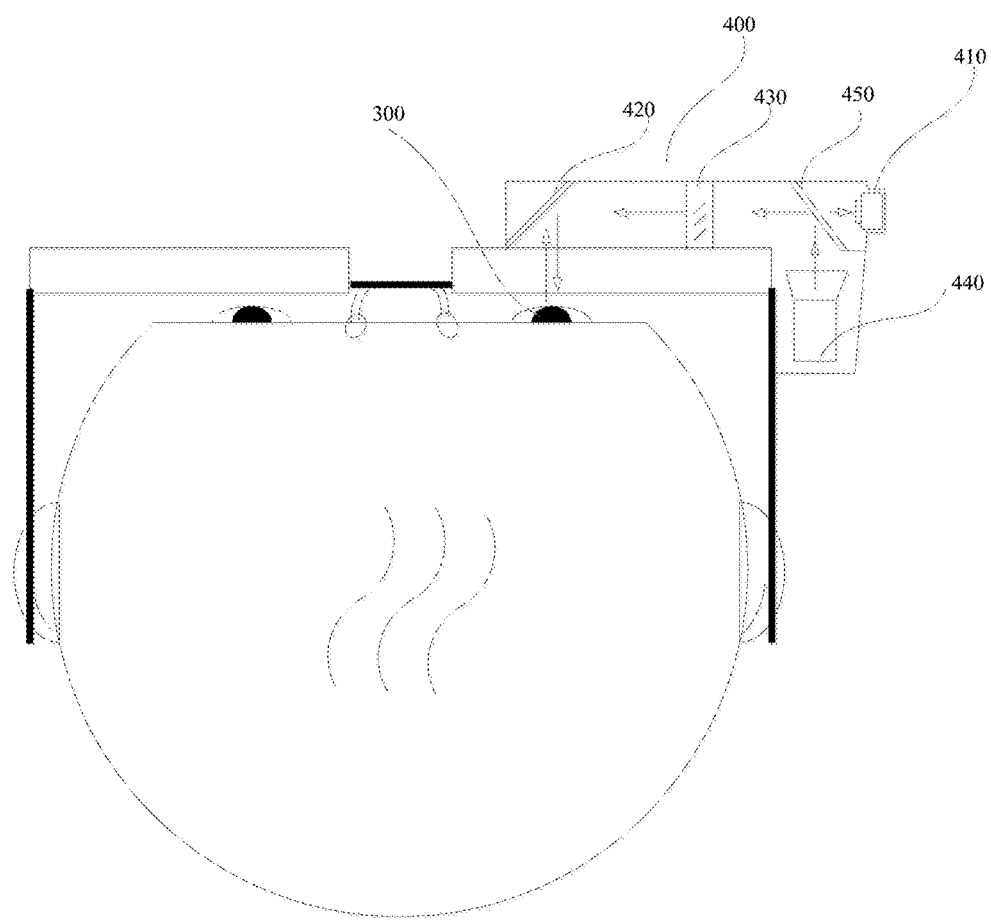
FIG. 4 shows an example schematic diagram of a specific example when an eye focusing point detection system is applied to an eyeglass according to an embodiment of the present application.

FIG. 4 shows a schematic diagram of a specific example when the eye focusing point detection system is applied to an eyeglass.

Here, a miniature camera 410, with the same function as the image collecting device in FIG. 3b, is arranged on the right outer side of the eyeglass in order not to affect the user to normally view the object;

a first light splitter 420, with the same function as the first light splitting unit in FIG. 3b, is arranged at a certain inclination on an intersection point of the direction of line-of-sight of the eye and the emergent direction of the camera 410, to transmit the light of the gazed object into the eye 300 and reflect the light from the eye 300 to the camera 410; and a lens with an adjustable focal length 430, with the same function as the lens with an adjustable focal length in FIG. 3b, is located between the first light splitter 420 and camera 410, to adjust the focal length value, so that the camera 410 can take a shot of the image that is on the fundus and with the definition greater than the preset value at a certain focal length value.

In this implementation manner, the image processing device is not shown in FIG. 4, and has the same function as the image processing device shown in FIG. 3b.

Because the brightness of the fundus is generally not enough, it is better to illuminate the fundus. In this implementation manner, the fundus is illuminated by a light emitting source 440. In order not to affect the user experience, the preferable light emitting source 440 here is a near-infrared light emitting source which has little influence on the eye 300 and to which the camera 410 is sensitive.

In this implementation manner, the light emitting source 440 is located on the outer side of the right eyeglass frame, and therefore a second light splitter 450 and the first light splitter 420 need to be used together to accomplish the transfer of the light emitted from the light emitting source 440 to the fundus. In this implementation manner, the second light splitter 450 is also located in front of the incident surface of the camera 410, and therefore, the light from the fundus to the second light splitter 450 also needs to be transmitted.

It can be seen that in this implementation manner, in order to improve the user experience and improve the collection definition of the camera 410, the first light splitter 420 may have features of high infrared reflectivity and high visible light transmittance. For example, the above features may be implemented by arranging an infrared reflective film on the side of the first light splitter 420 facing to the eye 300.

It can be seen from FIG. 4 that in this implementation manner, the eye focusing point detection system 400 is located on the side of the lens of the eyeglass far away from the eye 300, and therefore the lens may be regarded as a part of the eyeglass when the optical parameters of the eye are calculated, and in this case, it is unnecessary to know the optical features of the lens.

In other implementation manners of the embodiment of the present application, the eye focusing point detection system 400 may be located on the side of the lens of the eyeglass close to the eye 200, and in this case, it is required to obtain the optical feature parameters of the lens in advance and consider the influencing factors of the lens when the focus distance is calculated.

The light emitted from the light emitting source 440 is reflected by the second light splitter 450, projected by the lens with an adjustable focal length 430, reflected by the first light splitter 420, then transmitted into the eye of the user after passing through the lens of the glasses, and finally reaches the retina of the fundus; and the camera 410 takes a shot of the image on the fundus through the pupil of the eye 200 and via an optical path constituted by the first light splitter 420, the lens with an adjustable focal length 430 and the second light splitter 450.

Referring to FIG. 2*a*, the object determining unit 220 is generally an image processor, which may use an individually arranged GPU, or may be integrated into a same processor together with the image processing module (or the image processing device 330).

The processing unit 230 is configured to change a size of target imaging of the gazed object on the fundus of the user by optical zooming processing according to a predetermined zooming rule, and the components of the processing unit 230 are described below in detail for different situations.

Figure 2C:
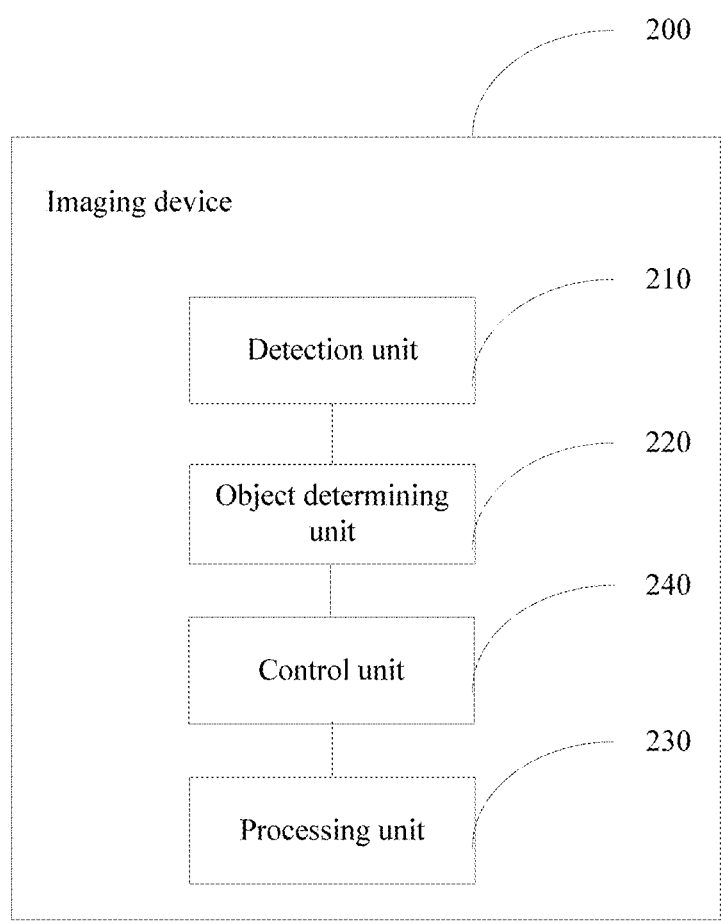
FIG. 2c shows an example schematic diagram of a module structure of an imaging device according to an embodiment of the present application.

In addition, for the purpose to avoid the change of imaging on the fundus of the user under a non-gazing state of the user, for example, in a random glancing process, to influence the user experience, referring to FIG. 2*c*, the imaging device 200 may further comprise: a control unit 240. The control unit 240 is configured to start the processing unit 230 when the user observes the gazed object for a duration exceeding a preset duration. Generally, the control unit 240 comprises a timer configured to monitor the duration of the focusing point of the eye of the user keeping at a constant position, or monitoring the gaze duration of the imaging at the central fovea of the macula lutea. It may be determined that the user is currently viewing the object if the duration of the focusing point of the eye of the user keeping at a constant position exceeds the preset duration or if the gaze duration of the imaging of a same object at the central fovea exceeds the preset duration, and therefore, the processing unit 230 may be started.

Figure 5A:
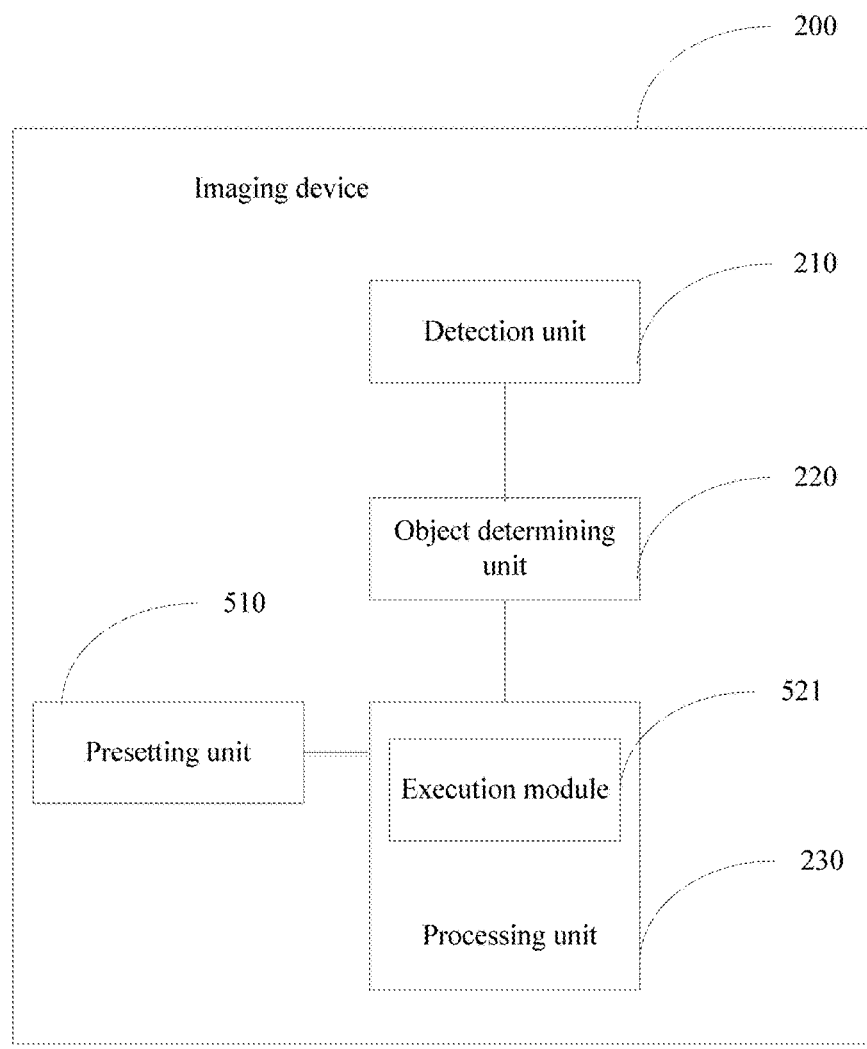
FIG. 5a shows an example schematic diagram of a module structure of a first implementation manner of the imaging device according to an embodiment of the present application.

The imaging device 200 is described below by implementation manners:

Referring to FIG. 5*a*, in a first implementation manner of the imaging device according to the embodiment, the device 200 further comprises: a presetting unit 510.

The presetting unit 510 is configured to preset a target focus distance of the eye of the user and a buffer of the target focus distance. Here, the target focus distance and the buffer may be set when the device 200 leaves factory, or may be set by the user according to personal preference. The setting manner may specifically be multiple manners such as pressing button, touch screen, voice control, and the like.

Correspondingly, the processing unit 230 comprises: an execution module 521.

The execution module 521 is configured to change the size of the target imaging according to the target focus distance, the actual focus distance and the buffer.

Specifically, the execution module 521 is configured to increase the actual focus distance to the target focus distance in the case where the actual focus distance is less than the target focus distance and the actual focus distance is outside the buffer, so as to reduce the target imaging; and configured to reduce the actual focus distance to the target focus distance in the case where the actual focus distance is greater than the target focus distance and the actual focus distance is outside the buffer, so as to magnify the target imaging. In addition, in some product applications, the buffer may not be set, that is, the buffer is set to be zero, in this case, the execution module 521 is configured to increase the actual focus distance to the target focus distance, in a situation that the actual focus distance is less than the target focus distance and the actual focus distance is outside the buffer, so as to reduce the target imaging; and configured to reduce the actual focus distance to the target focus distance, in a situation that the actual focus distance is greater than the target focus distance and the actual focus distance is outside the buffer, so as to magnify the target imaging.

It can be seen that the imaging device may magnify the image of the far and small gazed object on the fundus of the user, and may also reduce the image of the near and large gazed object on the fundus of the user, so as to facilitate the user to view the gazed object.

Figure 5B:
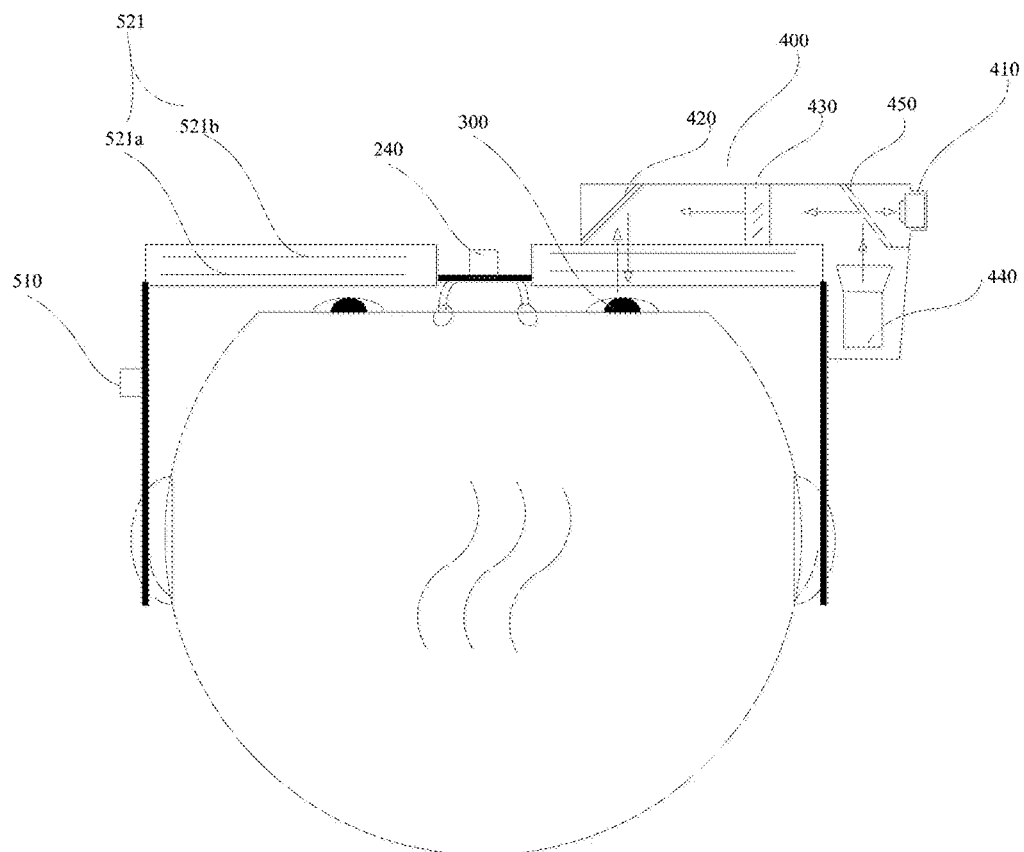
FIG. 5b shows an example schematic diagram of a specific example when the first implementation manner of the imaging device according to an embodiment of the present application is applied to an eyeglass.

FIG. 5*b* shows a schematic diagram of a specific example when the first implementation manner of the device according to the present application is applied to an eyeglass, wherein the eyeglass may be a common eyeglass, or may be an optical device such as a helmet or a wind shield. As shown in FIG. 5*b*, the eyeglass of this implementation manner uses the eye focusing point detection system 400 to implement the function of the detection unit 210, and the implementation of the eye focusing point detection system 400 is not described again herein.

In addition, the object determining unit 220 is not shown in FIG. 5*b*, and for the purpose of reducing the weight of the eyeglass and improving the portability thereof, the object determining unit 220 may be integrated into a processor together with an image processing device of the focusing point detection system 400.

The control unit 240 is arranged at a position between two lenses and configured to start the processing unit when the user observes the gazed object for a duration exceeding the preset duration.

The presetting unit 510 is arranged on a frame of the eyeglass (or may be arranged at another position), and may receive setting information in manners such as pressing button, touch screen, voice control, and the like.

The execution module 521 comprises a lens assembly that consists of at least two lenses in which at least one lens has adjustable imaging parameters. For simplicity, the execution subunit 521 in FIG. 5*b* comprises a first lens 521*a* close to the side of the eye, and a second lens 521*b* close to the side of the gazed object, and at least one lens in the first lens 521*a* and the second lens 521*b* has adjustable imaging parameters so as to change the size of the target imaging.

Here, the imaging parameter may be a focal length. With at least one lens with an adjustable imaging parameter denoted as an adjustable lens, the focal length of the adjustable lens may be adjusted as follows: 1) adjusting the focal length thereof by adjusting the curvature of at least one surface of the adjustable lens, for example, the adjustable lens comprises a cavity formed by a two-layer transparent layer, and the curvature may be adjusted by increasing or reducing a liquid medium in the cavity formed by the two-layer transparent layer, in this situation, the above information of changing the size of the target imaging, for example, may be reducing or increasing the liquid medium by a certain volume; or 2) adjusting the focal length thereof by adjusting the refractive index of the adjustable lens, for example, adjusting a voltage of an electrode corresponding to a liquid crystal medium which is filled in the adjustable lens, to adjust the arrangement of the liquid crystal medium, so as to change the refractive index of the adjustable lens, and in this situation, the above information of changing the size of the target imaging, for example, may be reducing or increasing the electrode voltage by a certain volume.

Besides the above focal length, the imaging parameters further comprise: a relative position between lenses. Here, the relative position between lenses may be changed by adjusting a relative position between the lenses along an optical axis direction, and/or a relative distance between the lenses in a direction perpendicular to the optical axis direction, and/or a relative turning angle of the lenses about the optical axis.

Here, the first lens 521a may be arranged such that the curvature of the side facing the eye of the user 300 is adjustable, the second lens 521b may be arranged such that the curvature of the side facing to the gazed object is adjustable, and the first lens 521a and the second lens 521b are arranged at fixed positions. Therefore, the eyeglass is simple in structure, and is light-weight and portable.

Figure 6A:
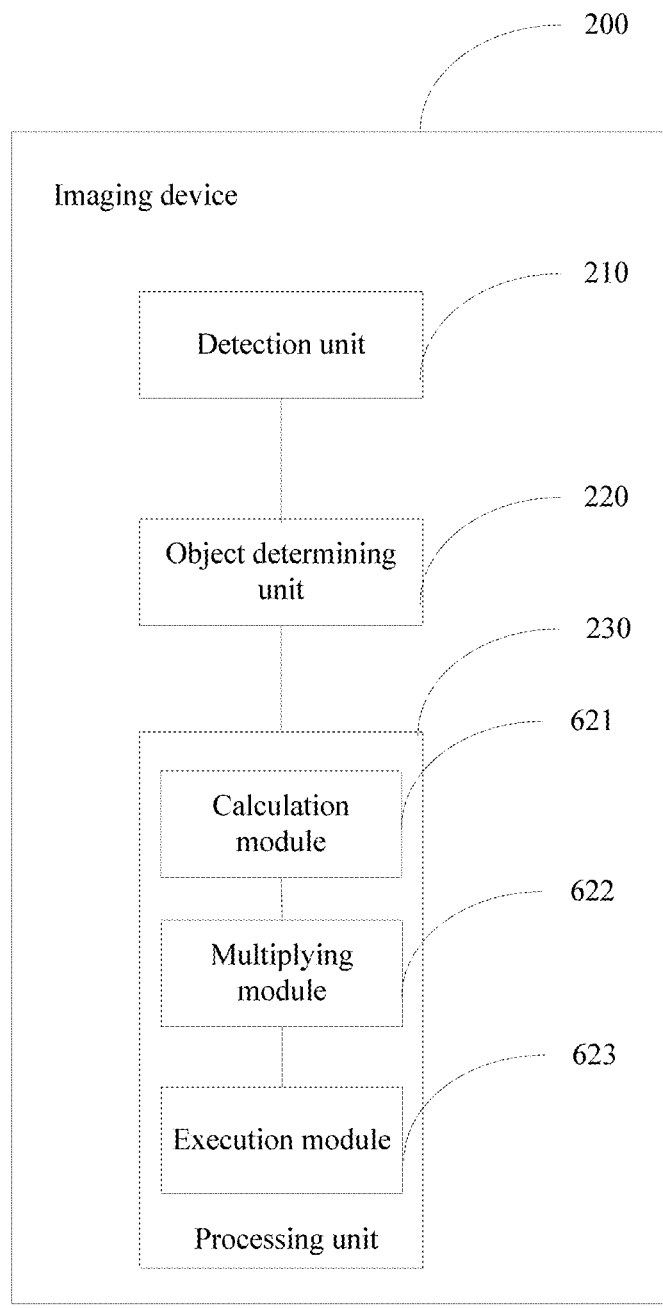
FIG. 6a shows an example schematic diagram of a module structure of a second implementation manner of the imaging device according to an embodiment of the present application.

Referring to FIG. 6a, in a second implementation manner of the imaging device according to the embodiment, the processing unit 230 of the device 200 comprises: a calculation module 621, a multiplying module 622 and an execution module 623.

The calculation module 621 is configured to calculate an actual area proportion of the target imaging on the fundus of the user. Here, the area of the fundus of the user is generally a fixed value, and after the image on the fundus of the user is collected by an image collecting module of the detection unit 210 or by an image collecting device of the eye focusing point detection system 400, the image on the central foveal of the macula lutea may be extracted to be used as the target imaging, so as to further acquire the area of the target imaging and then to obtain the actual area proportion of the target imaging on the fundus of the user.

The multiplying module 622 is configured to determine a corresponding magnification factor according to the actual area proportion.

The corresponding magnification factor may be determined according to the actual area proportion in multiple implementation manners, for example, the corresponding magnification factor is determined according to a piecewise function corresponding to the actual area proportion or by table look-up. In this implementation manner, a quick table look-up manner is selected, that is, a table of correspondence between the actual area proportion and the magnification factor is preset, and then during execution of the method, the current required magnification factor is determined by table look-up. Here, the correspondence table may be shown in Table 1, which is not described again herein.

The execution module 623 is configured to change the size of the target imaging according to the magnification factor.

Figure 6B:
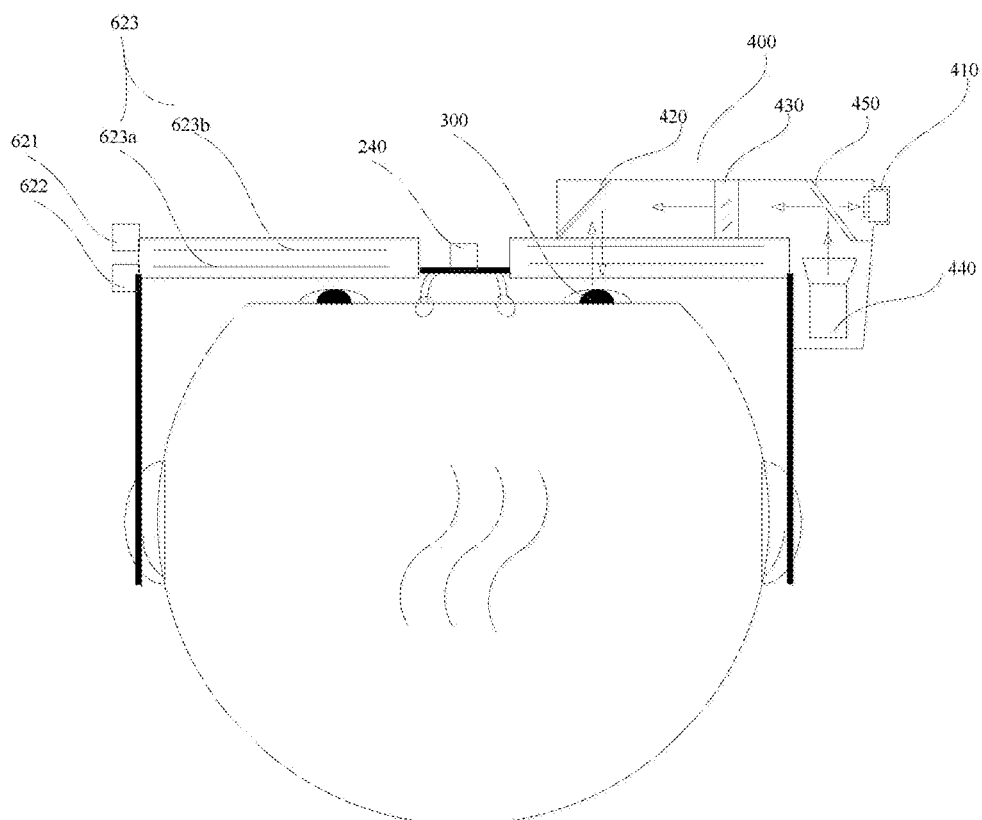
FIG. 6b shows an example schematic diagram of a specific example when the second implementation manner of the imaging device according to an embodiment of the present application is applied to an eyeglass.

FIG. 6b shows a schematic diagram of a specific example when the second implementation manner of the device according to the embodiment is applied to an eyeglass.

As shown in FIG. 6b, the eyeglass of this implementation manner also uses the eye focusing point detection system 400 to implement the function of the detection unit 210, and the implementation of the eye focusing point detection system 400 is not described again herein.

In addition, the object determining unit 220 is also not shown in FIG. 6b, and for the purpose of reducing the weight of the eyeglass and improving the portability thereof, the object determining unit 220 may be integrated into a processor together with an image processing device of the focusing point detection system 400.

A calculation subunit 621 and a multiplying subunit 622 are individually arranged on one side of a left lens (or may be arranged on other positions), and respectively configured to calculate a actual area proportion of the target imaging on the fundus of the user and determining a corresponding magnification factor according to the actual area proportion. Here, the calculation subunit 621 and the multiplying subunit 622 may be integrated together, or further, the functions of the calculation subunit 621, the multiplying subunit 622, the object determining unit 220 and the image processing device are implemented by a processor, so as to reduce the weight of the eyeglass. When the multiplying subunit 622 determines the magnification factor by table look-up, it should further comprise a memory configured to store the correspondence table.

The execution subunit 623 is basically the same as that in the previous implementation manner. For simplicity, in FIG. 6b, the execution subunit 623 comprises a first lens 623a close to the side of the eye, and a second lens 623b close to the side of the gazed object, and at least one lens in the first lens 623a and the second lens 623b has adjustable imaging parameters. The implementation principle of the execution subunit 623 is basically the same as that in the previous implementation manner, which is not described again herein.

Figure 7A:
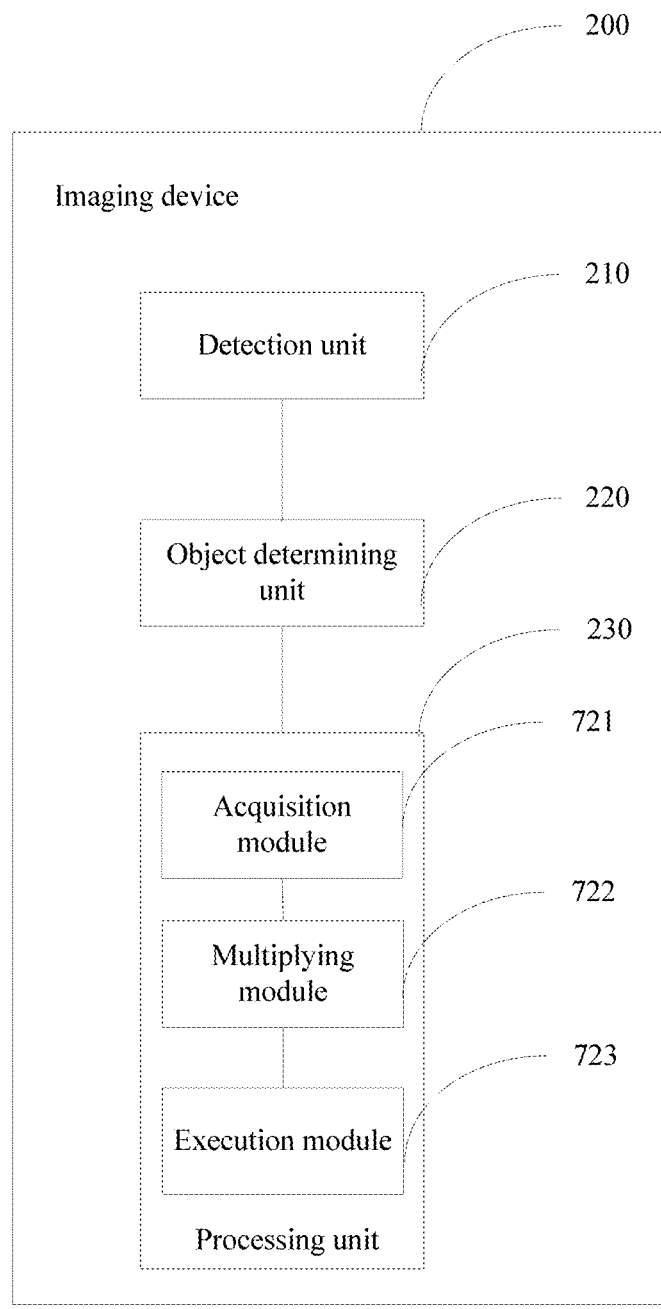
FIG. 7a shows an example schematic diagram of a module structure of a third implementation manner of the imaging device according to an embodiment of the present application.

Referring to FIG. 7a, in a third implementation manner of the imaging device according to the embodiment, the processing unit 230 of the device 200 comprises: an acquisition module 721, a multiplying module 722 and an execution module 723.

Figure 7B:
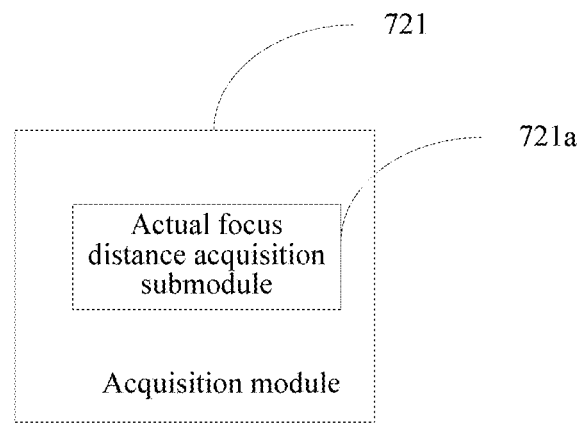
FIG. 7b shows an example schematic diagram of a module structure of an acquisition module according to an embodiment of the present application.

The acquisition module 721 is configured to acquire a viewing distance from the gazed object to the eye of the user. The acquisition module 721 may have multiple implementation manners as follows:

Referring to FIG. 7b, in an optional implementation manner, the acquisition module 721 comprises: an actual focus distance acquisition submodule 721a configured to acquire the actual focus distance and taking the actual focus distance as the viewing distance from the gazed object to the eye of the user.

Figure 7C:
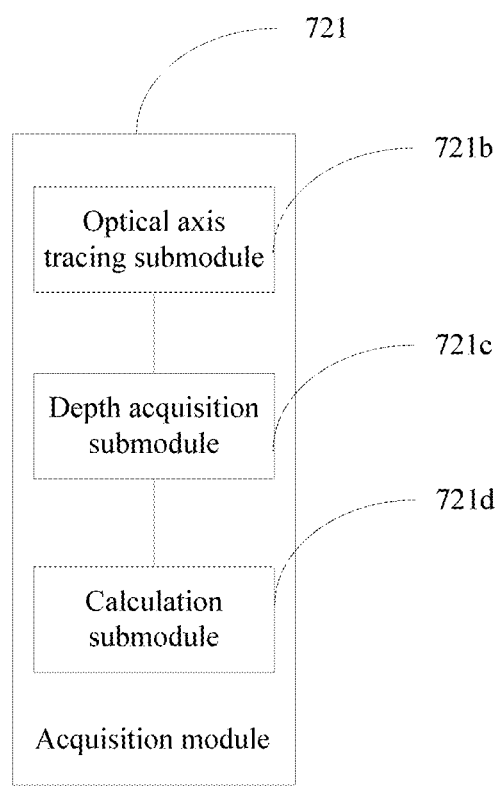
FIG. 7c shows an example schematic diagram of another module structure of the acquisition module according to an embodiment of the present application.

Alternatively, referring to FIG. 7c, in another optional implementation manner, the acquisition module 721 comprises:

an optical axis tracing submodule 721b configured to trace the direction of line-of-sight of the eye of the user;

a depth acquisition submodule 721c configured to acquire a scene depth of the position of the gazed object according to the direction of line-of-sight; and a calculation submodule 721d configured to calculate the viewing distance from the gazed object to the eye of the user according to the scene depth.

Figure 7D:
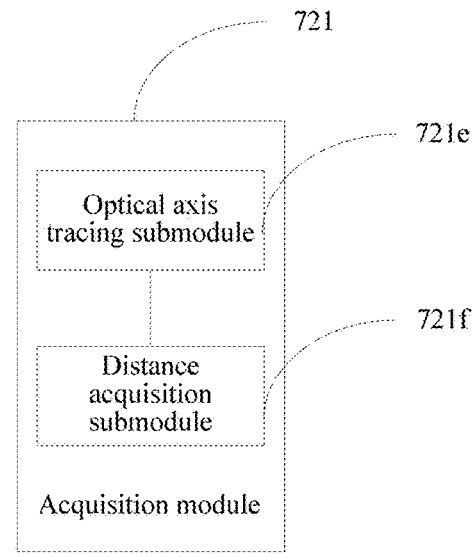
FIG. 7d shows an example schematic diagram of still another module structure of the an acquisition module according to an embodiment of the present application.

Alternatively, referring to FIG. 7d, in another optional implementation manner, the acquisition module 721 comprises:

an optical axis tracing submodule 721e configured to trace direction of line-of-sight of two eyes of the user, and a distance acquisition submodule 721f configured to obtain the viewing distance from the gazed object to the eye of the users according to an intersection point of line-of-sight of the two eyes of the user.

Referring to FIG. 7a, the multiplying module 722 is configured to determine a corresponding magnification factor according to the viewing distance.

The multiplying module 722 may have multiple implementation manners, for example, determine the corresponding magnification factor according to a piecewise function of the corresponding viewing distance or by table look-up. In this implementation manner, a quick table look-up manner is selected, that is, a table of correspondence between the viewing distance and the magnification factor is preset, and then during execution, the current required magnification factor is determined by table look-up. The table of correspondence between the viewing distance and the magnification factor is shown in Table 2, which is not described again herein.

The execution module 723 is configured to change the size of the target imaging according to the magnification factor.

Figure 7E:
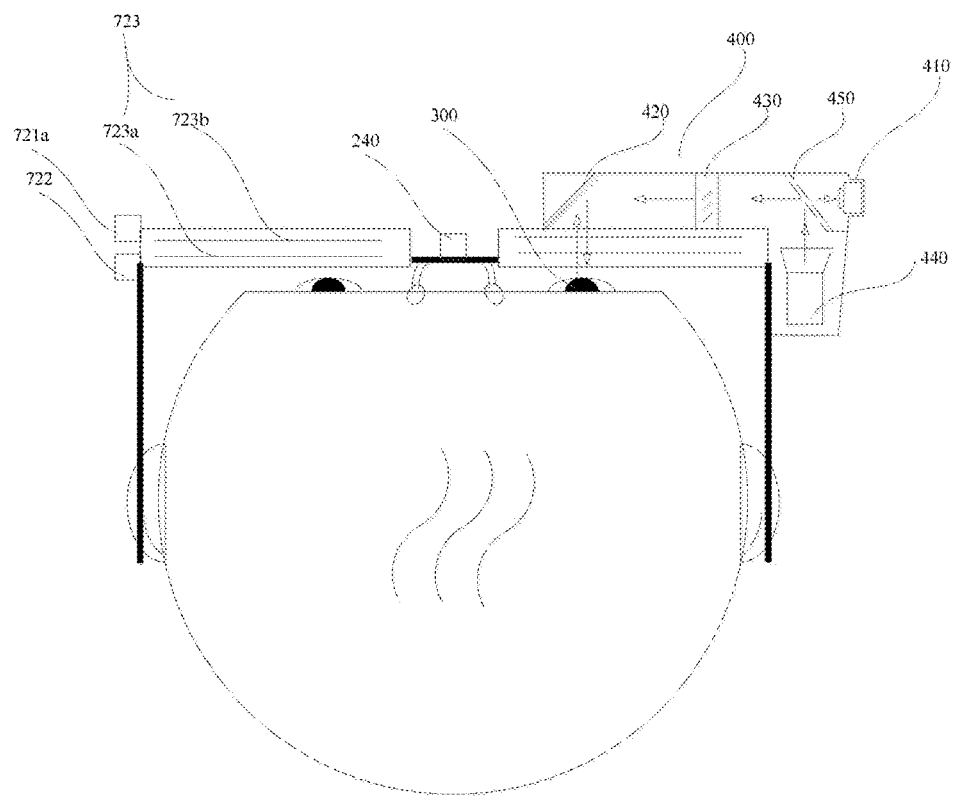
FIG. 7e shows an example schematic diagram of a specific example when the third implementation manner of the imaging device is applied to an eyeglass according to an embodiment of the present application.

FIG. 7e shows a schematic diagram of a specific example when the third implementation manner of the device according to the present application is applied to an eyeglass. The eyeglass also uses the eye focusing point detection system 400 to implement the function of the detection unit 210, and the implementation of the eye focusing point detection system 400 is not described again herein. Moreover, the acquisition module 721 preferably uses an actual focus distance acquisition submodule 721a, so as to implement acquisition of the viewing distance from the gazed object to the eye of the user by means of the actual focus distance measured by the eye focusing point detection system 400.

In FIG. 7e, the multiplying module 722 is arranged individually and configured to determine the corresponding magnification factor according to the viewing distance. Here, the multiplying module 722 and an image processing device of the eye focusing point detection system 400 may be integrated into a processor.

In addition, the execution subunit 723 comprises: a first lens 723a close to one side of the eye and a second lens 723b close to the side of the gazed object, and at least one lens in the first lens 723a and the second lens 723b has adjustable imaging parameters so as to change the size of the target imaging according to the magnification factor, and the specific implementation principle is not described again herein.

Figure 8A:
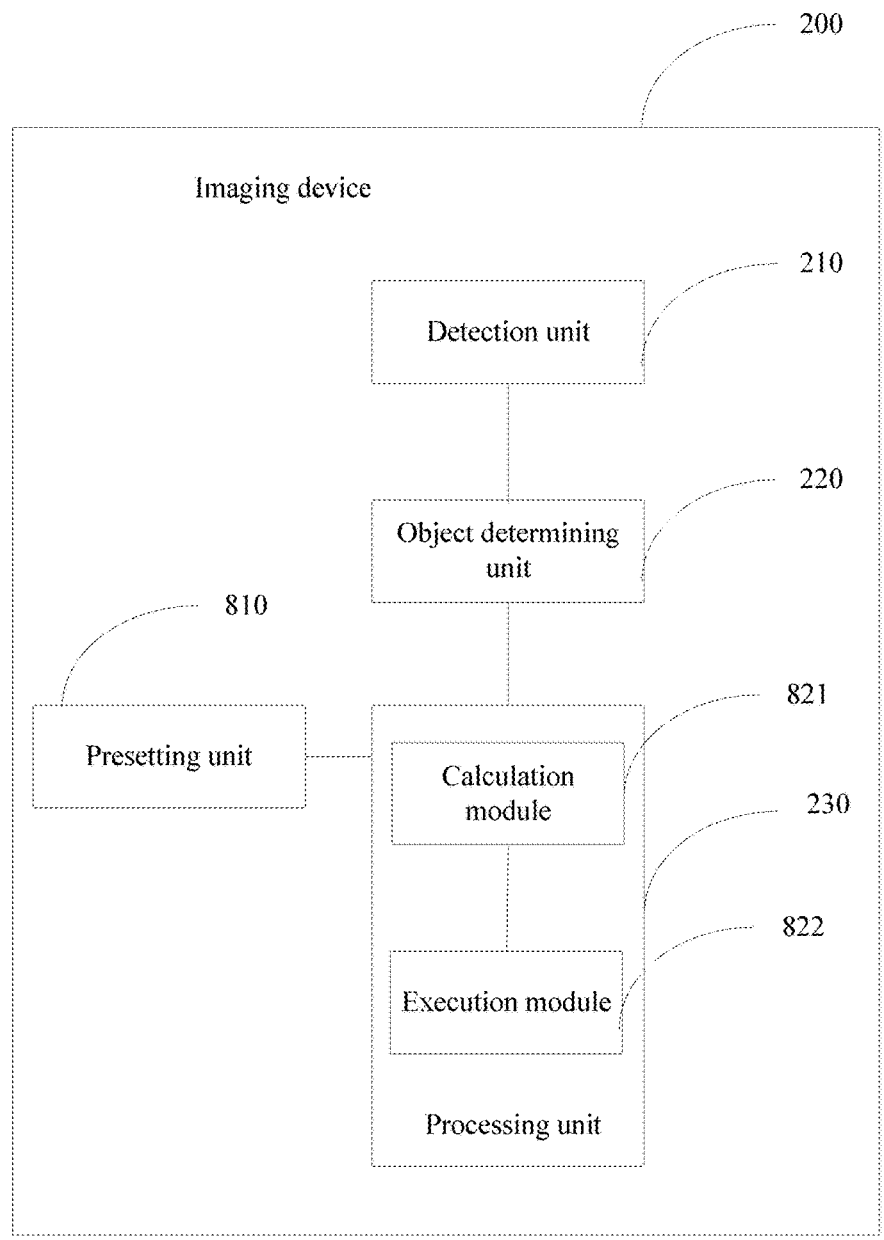
FIG. 8a shows an example schematic diagram of a module structure of a fourth implementation manner of the imaging device according to an embodiment of the present application.

Referring to FIG. 8a, in a fourth implementation manner of the imaging device according to the embodiment, the device 200 further comprises: a presetting unit 810.

The presetting unit 810 is configured to preset a target area proportion of the target imaging and a buffer of the target area proportion. Here, the target area proportion and the buffer may be set when the device 200 leaves factory, or may be set by the user according to personal preference. The setting manner may specifically be multiple manners such as pressing button, touch screen, voice control, and the like.

Correspondingly, the processing unit 230 comprises: a calculation module 821 and an execution module 822.

The calculation module 821 is configured to calculate an actual area proportion of the target imaging on the fundus of the user.

Here, the area of the fundus of the user is generally a fixed value, and after the image on the fundus of the user is collected by an image collecting module of the detection unit 210 or by an image collecting device of the eye focusing point detection system, the image on the central foveal of the macula lutea may be extracted to be used as the target imaging, so as to further acquire the area of the target imaging and then to obtain the actual area proportion of the target imaging on the fundus of the user.

The execution module 822 is configured to change the size of the target imaging according to the target area proportion, the actual area proportion and the buffer.

Specifically, the execution module 822 is configured to magnify the target imaging to the target area proportion in the case where the actual area proportion is less than the target area proportion and the actual area proportion is outside the buffer; and reduce the target imaging to the target area proportion in the case where the actual area proportion is greater than the target area proportion and the actual area proportion is outside the buffer. In addition, in some product applications, the buffer may not be set, which is equivalent to that the buffer is set to zero, and in this case, the execution module 822 is configured to magnify the target imaging to the target area proportion in the case where the actual area proportion is less than the target area proportion; and reduce the target imaging to the target area proportion in the case where the actual area proportion is greater than the target area proportion.

Figure 8B:
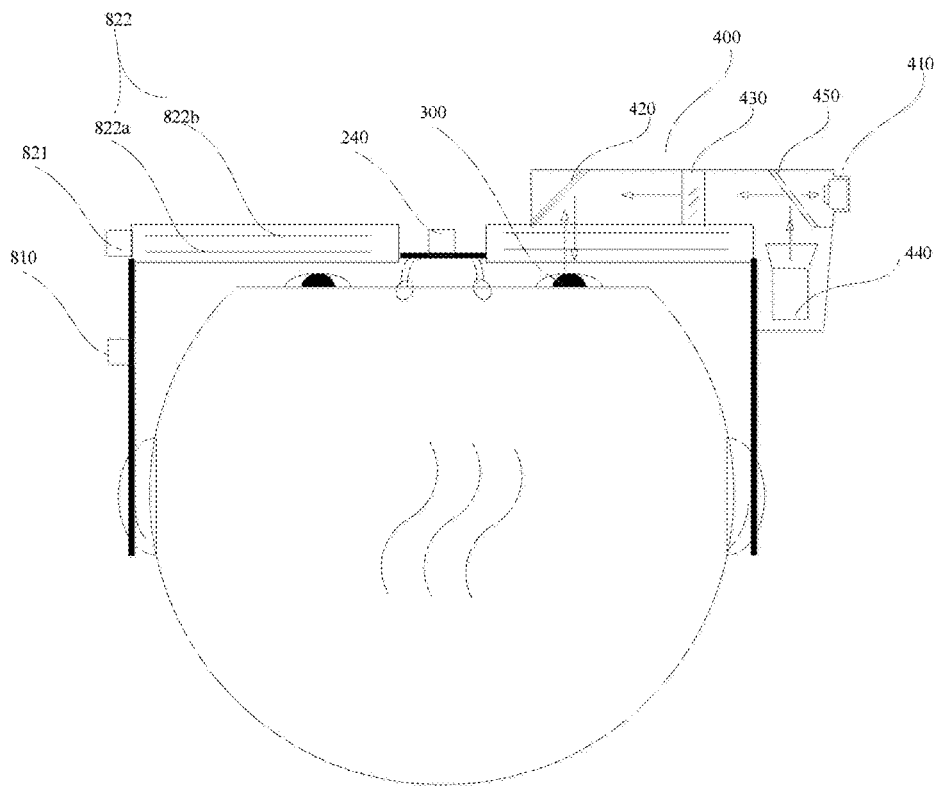
FIG. 8b shows an example schematic diagram of a specific example when the fourth implementation manner of the imaging device is applied to an eyeglass according to an embodiment of the present application.

FIG. 8b shows a schematic diagram of a specific example when the fourth implementation manner of the imaging device according to the embodiment is applied to an eyeglass.

As shown in FIG. 8b, the eyeglass also uses the eye focusing point detection system 400 to implement the function of the detection unit 210, and the implementation of the eye focusing point detection system 400 is not described again herein. The object determining unit 220 is not shown in the FIG. 8b, and for the purpose of reducing the weight of the eyeglass and improving the portability thereof, the object determining unit 220 may be integrated into a processor together with an image processing device of the focusing point detection system 400.

The presetting unit 810 is arranged on a frame of the eyeglass (or may be arranged at another position), and may receive setting information in manners such as pressing button, touch screen, voice control, and the like.

The control unit 240 is arranged at a position between two lenses and configured to start the processing unit 230 in the case where the user observes the gazed object for a duration exceeding the preset duration.

The processing unit 230 comprises a calculation module 821 arranged at one side of the left lens, and an execution module 822 arranged inside the lens.

Here, the calculation module 821 and the object determining unit 220 may be implemented using a same processor, or the calculation module 821, the object determining unit 220 and the image processing device of the eye focusing point detection system 400 are integrated into one processor, so as to simplify the structure of the eyeglass.

The execution module 822 comprises a lens assembly that consists of at least two lenses in which at least one lens has adjustable imaging parameters. For simplicity, the execution module 822 in FIG. 8b comprises: a first lens 822a close to the side of the eye and a second lens 822b close to the side of the gazed object, and at least one lens in the first lens 822a and the second lens 822b has adjustable imaging parameters so as to change the size of the target imaging, and the specific implementation principle is not described again herein.

Figure 9:
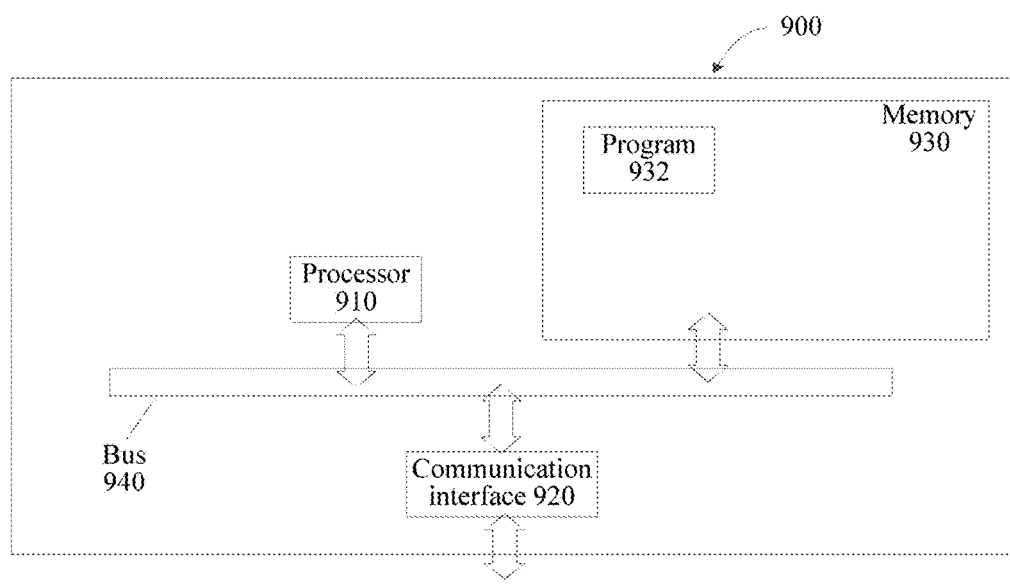
FIG. 9 shows an example structural diagram of the imaging device according to an embodiment of the present application.

The structure of the imaging device of the embodiment of the present invention is shown in FIG. 9. The specific embodiment of the present invention is not intended to limit the specific implementation of the imaging device, as shown in FIG. 9, the imaging device 900 may comprise:

a processor 910, a Communications Interface 920, a memory 930 and a communication bus 940. Wherein:

The processor 910, the communications interface 920 and the memory 930 complete the mutual communication through the communication bus 940.

The communications interface 920 is configured to communicate with other network elements.

The processor 910 is configured to implement the program 932, specifically, it can implement the relevant steps in the method embodiment shown in FIG. 9 above.

Specifically, the program 932 may comprise the program codes which comprise the computer operating instructions.

The processor 910 may be a Central Processing Unit CPU, or a specific integrated circuit ASIC (Application Specific Integrated Circuit), or one or more integrated circuits configured to implement the embodiment of the present invention.

The memory 930 is configured to store the program 932. The memory 930 may contain a high-speed RAM memory and may also comprise a non-volatile memory, such as at least one disk memory. Specifically, the program 932 may execute the following steps:

detecting a position of a focusing point of an eye of a user;

determining, according to the position of the focusing point, an object gazed by the user; and changing a size of target imaging of the gazed object on the fundus of the user according to a predetermined zooming rule.

Configured to the specific implementation of the steps in the program 932, see the corresponding steps or modules in the above-mentioned embodiment, and the details are not described here. It may be clearly understood by persons skilled in the art that, configured to the purpose of convenient and brief description, configured to the detailed working process of the above mentioned device and module, refer to the corresponding process description in the above-mentioned method embodiment, and the details are not described here again. In summary, in the device of the embodiment, the user's fundus images of the gazing object can be scaled in a local scaling mode, so as to avoid changing the overall view of the user and to enable the user to conveniently observe the gazing object and to simultaneously correctly perceive the surrounding environment.

In summary, in the imaging device according to the embodiment, an object gazed by a user is determined according to a position of a focusing point of an eye of the user, and a size of target imaging of the gazed object on the fundus of the user is automatically changed by optical zooming processing according to the size of the target imaging of the gazed object on the fundus of the user or according to a viewing distance from the gazed object to the eye of the user, so that the user can observe the gazed object at a modest distance and with a moderate size of the imaging on the fundus, and therefore it is convenient for the user to observe the gazed object.

A person skilled in the art should be aware that, in combination with the examples described in the embodiments here, units and algorithm steps can be implemented by electronic hardware, or a combination of computer software and electronic hardware. Whether the functions are executed by hardware or software depends on the particular applications and design constraint conditions of technical solutions. A person skilled in the art may use different methods to implement the described functions for each particular application, but it should not be considered that the implementation goes beyond the scope of the present application.

When being implemented in the form of a software functional unit and sold or used as a separate product, the functions may be stored in a computer-readable storage medium. Based on such understanding, the part of the technical solutions of the present application which contributes to the prior art or the part of the technical solutions may be embodied in a form of a computer software product, and the computer software product is stored in a memory medium, and contains various instructions for causing a computer apparatus (which may be a personal computer, a server, a network apparatus, or the like) to execute all the steps or part of the steps of the methods of individual embodiments of the present application. The storage medium includes any medium that may store program code, such as a USB flash drive, a removable hard disk, a read-only memory (ROM), a random access memory (RAM), a magnetic disk, or an optical disc.

The above implementation manners are used only to describe the present application, and are not intended to limit the present application. A person of ordinary skill in the art will make variations and modifications without departing from the spirit and scope of the present application. Therefore, all the equivalent technical solutions also fall within the range of the present application, and the scope of protection of the present application shall be limited by the claims.

The invention claimed is:

1. A method, comprising:

detecting, by a system comprising a processor, a position of a focusing point of an eye of a user, determining, according to the position of the focusing point, a gazed object gazed by the user; and changing a size of target imaging of the gazed object on a fundus of the user according to a predetermined zooming rule, wherein the detecting the position of the focusing point of the eye of the user comprises:

collecting images on the fundus of the user;

adjusting an imaging parameter of an optical path between the eye and an image collecting position to collect a set of images with a definition greater than a preset value;

processing the images to obtain an equivalent focal length and a direction of line-of-sight of the eye that are corresponding to the set of images with the definition greater than the preset value;

obtaining an actual focus distance of the eye according to the equivalent focal length of the eye; and obtaining the position of the focusing point according to the direction of line-of-sight and the actual focus distance.

2. The method of claim 1, wherein the changing the size of the target imaging of the gazed object on the fundus of the user according to the predetermined zooming rule comprises:

in the case where the user observes the gazed object for a duration exceeding a preset duration, changing the size of the target imaging of the gazed object on the fundus of the user according to the predetermined zooming rule.

3. The method of claim 1, wherein the processing the images to obtain the equivalent focal length and the direction of line-of-sight of the eye that are corresponding to the set of images with the definition greater than the preset value comprises:

analyzing the images to determine the set of images with the definition greater than the preset value; and determining the equivalent focal length and the direction of line-of-sight of the eye according to the set of images with the definition greater than the preset value and the imaging parameter of the optical path corresponding to the set of images with the definition greater than the preset value.

4. The method of claim 1, wherein the method further comprises:

presetting a target focus distance of the eye of the user and a buffer of the target focus distance, wherein, the changing the size of the target imaging of the gazed object on the fundus of the user according to the predetermined zooming rule comprises:
    changing the size of the target imaging according to the target focus distance, the actual focus distance and the buffer.

5. The method of claim 4, wherein the changing the size of the target imaging according to the target focus distance, the actual focus distance and the buffer comprises:
    in the case where the actual focus distance is determined to be less than the target focus distance and the actual focus distance is determined to be outside the buffer, increasing the actual focus distance to the target focus distance.

6. The method of claim 4, wherein the changing the size of the target imaging according to the target focus distance, the actual focus distance and the buffer comprises:
    in the case where the actual focus distance is determined to be greater than the target focus distance and the actual focus distance is determined to be outside the buffer, reducing the actual focus distance to the target focus distance.

7. The method of claim 4, wherein the buffer is zero.

8. The method of claim 1, wherein the changing the size of the target imaging of the gazed object on the fundus of the user according to the predetermined zooming rule comprises:
    determining an actual area proportion of the target imaging on the fundus of the user;
    determining a corresponding magnification factor according to the actual area proportion; and
    changing the size of the target imaging according to the corresponding magnification factor.

9. The method of claim 1, wherein the changing the size of the target imaging of the gazed object on the fundus of the user according to the predetermined zooming rule comprises:
    acquiring a viewing distance from the gazed object to the eye of the user,
    determining a corresponding magnification factor according to the viewing distance; and
    changing the size of the target imaging according to the corresponding magnification factor.

10. The method of claim 9, wherein the acquiring the viewing distance from the gazed object to the eye of the user comprises:
    using the actual focus distance as the viewing distance from the gazed object to the eye of the user.

11. The method of claim 9, wherein the position of the focusing point is a first position, and wherein the acquiring the viewing distance from the gazed object to the eye of the user comprises:
    tracing the direction of line-of-sight of the eye of the user, acquiring a scene depth of a second position of the gazed object according to the direction of line-of-sight, and determining the viewing distance from the gazed object to the eye of the user according to the scene depth.

12. The method of claim 9, wherein the acquiring the viewing distance from the gazed object to the eye of the user comprises:
    tracing the directions of line-of-sight of two eyes of the user, and obtaining the viewing distance from the gazed object to the eye of the user according to an intersection point of the directions of line-of-sight of the two eyes of the user.

13. The method of claim 1, wherein the method further comprises:
    presetting a target area proportion of the target imaging and a buffer of the target area proportion, wherein,
    the changing the size of the target imaging of the gazed object on the fundus of the user according to a predetermined zooming rule comprises:
    determining an actual area proportion of the target imaging on the fundus of the user; and
    changing the size of the target imaging according to the target area proportion, the actual area proportion and the buffer.

14. The method of claim 13, wherein the changing the size of the target imaging according to the target area proportion, the actual area proportion and the buffer comprises:
    in the case where the actual area proportion is determined to be less than the target area proportion, and the actual area proportion is determined to be outside the buffer, magnifying the target imaging to the target area proportion.

15. The method of claim 13, wherein the changing the size of the target imaging according to the target area proportion, the actual area proportion and the buffer comprises:
    in the case where the actual area proportion is determined to be greater than the target area proportion, and the actual area proportion is determined to be outside the buffer, reducing the target imaging to the target area proportion.

16. The method of claim 13, wherein the buffer is zero.

17. The method of claim 1, wherein the changing the size of the target imaging of the gazed object on the fundus of the user according to the predetermined zooming rule comprises:
    changing the size of the target imaging of the gazed object on the fundus of the user by optical zooming processing.

18. An imaging device, comprising:
    a processor that executes or facilitates execution of executable units to perform operations of the imaging device, the executable units comprising:
    a detection unit configured to detect a position of a focusing point of an eye of a user;
    an object determining unit configured to determine, according to the position of the focusing point, a gazed object at which the user is determined to be gazing; and
    a processing unit configured to change a size of target imaging of the gazed object on a fundus of the user according to a predetermined zooming rule,
    wherein the detection unit comprises:
        an image collecting module configured to collect images on the fundus of the user;
        an adjustment module configured to adjust an imaging parameter of an optical path between the eye and the image collecting module to collect a set of images with a definition greater than a preset value;
        an image processing module configured to process the images to obtain an equivalent focal length and a direction of line-of-sight of the eye that are corresponding to the set of images with the definition greater than the preset value;
        a distance obtaining module configured to obtain an actual focus distance of the eye according to the equivalent focal length of the eye; and
        a position obtaining module configured to obtain the position of the focusing point according to the direction of line-of-sight and the actual focus distance.

19. The imaging device of claim 18, wherein the executable units further comprises:
a control unit configured to start the processing unit in the case where the user is determined to be observing the gazed object for a duration exceeding a preset duration.

20. The imaging device of claim 18, wherein the image processing module comprises:
an image analysis submodule configured to analyze the images to determine the set of images with the definition greater than the preset value; and
a calculation submodule configured to determine the equivalent focal length and the direction of line-of-sight of the eye according to the set of images with the definition greater than the preset value and the imaging parameter of the optical path corresponding to the set of images with the definition greater than the preset value.

21. The imaging device of claim 18, wherein the executable units further comprises:
a presetting unit configured to preset a target focus distance of the eye of the user and a buffer of the target focus distance, wherein,
the processing unit comprises an execution module configured to change the size of the target imaging according to the target focus distance, the actual focus distance and the buffer.

22. The imaging device of claim 18, wherein the processing unit comprises:
a calculation module configured to determine an actual area proportion of the target imaging on the fundus of the user;
a multiplying module configured to determine a corresponding magnification factor according to the actual area proportion; and
an execution module configured to change the size of the target imaging according to the corresponding magnification factor.

23. The imaging device of claim 18, wherein the processing unit comprises:
an acquisition module configured to acquire a viewing distance from the gazed object to the eye of the user,
a multiplying module configured to determine a corresponding magnification factor according to the viewing distance; and
an execution module configured to change the size of the target imaging according to the corresponding magnification factor.

24. The imaging device of claim 23, wherein the acquisition module comprises:
an actual focus distance acquisition submodule configured to acquire the actual focus distance, and using the actual focus distance as the viewing distance from the gazed object to the eye of the user.

25. The imaging device of claim 23, wherein the acquisition module comprises:
an optical axis tracing submodule configured to trace the direction of line-of-sight of the eye of the user,
a depth acquisition submodule configured to acquire a scene depth of the position of the gazed object according to the direction of line-of-sight; and
a viewing distance submodule configured to determine the viewing distance from the gazed object to the eye of the user according to the scene depth.

26. The imaging device of claim 23, wherein the acquisition module comprises:
an optical axis tracing submodule configured to trace directions of line-of-sight of two eyes of the user, and
a viewing distance submodule configured to obtain the viewing distance from the gazed object to the eye of the user according to an intersection point of the directions of line-of-sight of the two eyes of the user.

27. The imaging device of claim 18, wherein the executable units further comprises:
a presetting unit configured to preset a target area proportion of the target imaging and a buffer of the target area proportion, wherein,
the processing unit comprises:
a calculation module configured to determine an actual area proportion of the target imaging on the fundus of the user; and
an execution module configured to change the size of the target imaging according to the target area proportion, the actual area proportion and the buffer.

28. The imaging device of claim 18, wherein the imaging device is an eyeglass.

29. A computer-readable storage device, comprising at least one executable instruction, which, in response to execution, causes an imaging device comprising a processor to perform operations, comprising:
detecting a position of a focusing point of an eye of a user,
determining, according to the position of the focusing point, an object gazed at by the user, and
changing a size of target imaging of the object on a fundus of the user according to a predetermined zooming rule,
wherein the detecting the position of the focusing point of the eye of the user comprises:
collecting images on the fundus of the user,
adjusting an imaging parameter of an optical path between the eye and an image collecting position to collect a set of images with a definition greater than a preset value;
processing the images to obtain an equivalent focal length and a direction of line-of-sight of the eye that are corresponding to the set of images with the definition greater than the preset value;
obtaining an actual focus distance of the eye according to the equivalent focal length of the eye; and
obtaining the position of the focusing point according to the direction of line-of-sight and the actual focus distance.

30. An imaging device, comprising a processor and a memory, wherein the memory stores at least one executable instruction, the processor is connected to the memory via a communication bus, and when the imaging device is in operation, the processor executes or facilitates execution of the at least one executable instruction stored in the memory, to cause the imaging device to execute operations, comprising:
detecting a position of a focusing point of an eye of a user,
determining, according to the position of the focusing point, a gazed object at which the user has been determined to be gazing; and
changing a size of target imaging of the gazed object on a fundus of the user according to a predetermined zooming rule,
wherein the detecting the position of the focusing point of the eye of the user comprises:
collecting images on the fundus of the user,
adjusting an imaging parameter of an optical path between the eye and an image collecting position to collect a set of images with a definition greater than a preset value;
processing the images to obtain an equivalent focal length and a direction of line-of-sight of the eye that are corresponding to the set of images with the definition greater than the preset value;

obtaining an actual focus distance of the eye according to the equivalent focal length of the eye; and obtaining the position of the focusing point according to the direction of line-of-sight and the actual focus distance.

* * * * *